US010590436B2

United States Patent
Meijrink et al.

(10) Patent No.: US 10,590,436 B2
(45) Date of Patent: *Mar. 17, 2020

(54) CRISPR-CAS SYSTEM FOR A LIPOLYTIC YEAST HOST CELL

(71) Applicant: DSM IP ASSETS B.V., Heerlen (NL)

(72) Inventors: Bernard Meijrink, Echt (NL); René Verwaal, Echt (NL); Bianca Elisabeth Maria Gielesen, Echt (NL); Johannes Andries Roubos, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/541,288

(22) PCT Filed: Jan. 6, 2016

(86) PCT No.: PCT/EP2016/050135
§ 371 (c)(1),
(2) Date: Jun. 30, 2017

(87) PCT Pub. No.: WO2016/110511
PCT Pub. Date: Jul. 14, 2016

(65) Prior Publication Data
US 2018/0023096 A1    Jan. 25, 2018

Related U.S. Application Data

(60) Provisional application No. 62/177,497, filed on Mar. 16, 2015.

(30) Foreign Application Priority Data

Jan. 6, 2015 (EP) ..................................... 15150135
Jan. 6, 2015 (EP) ..................................... 15150148

(51) Int. Cl.
| | | |
|---|---|---|
| C12P 19/34 | (2006.01) | |
| C12N 15/64 | (2006.01) | |
| C07H 21/02 | (2006.01) | |
| C12N 15/90 | (2006.01) | |
| C12N 15/63 | (2006.01) | |
| C12N 9/22 | (2006.01) | |
| C12N 15/11 | (2006.01) | |

(52) U.S. Cl.
CPC ............. *C12N 15/905* (2013.01); *C12N 9/22* (2013.01); *C12N 15/11* (2013.01); *C12N 15/63* (2013.01); *C12N 2310/20* (2017.05)

(58) Field of Classification Search
CPC ........ A61K 38/00; C07K 16/30; C12N 15/10; C12N 15/86; C12N 15/81
See application file for complete search history.

(56) References Cited

U.S. PATENT DOCUMENTS

2018/0010151 A1* 1/2018 Verwaal ............... C12N 15/102

OTHER PUBLICATIONS

Ryan et al., eLife, 2014; 3: 1-15.*
Hoppner (Horm Re. 2002, 58 Suppl. 3:7-15) (Year: 2002).*
Ryan, et al., "Multiplex Engineering of Industrial Yeast Genomes Using CRISPRm," Methods in Enzymology, (2014) vol. 546: 473-489.
Bao, et al., "Homology-Integrated CRISPR-Cas (HI-CRISPR) System for One-Step Multigene Disruption in *Saccharomyces cerevisiae*," ACS Synthetic Biology (2014).
Madzak, et al., "Heterologous protein expression and secretion in the non-conventional yeast *Yarrowia lipolytica*: a review," Journal of Biotechnology, (2004) vol. 109: 63-81.
Zhang, et al., "Construction of a Quadruple Auxotrophic Mutant of an Industrial Polyploid *Saccharomyces cerevisiae* Strain by Using RNA-Guided Cas9 Nuclease," Applied and Environmental Microbiology, (2014) vol. 80, No. 24: 1694-7701.
Dicarlo, et al., "Genome engineering in *Saccharomyces cerevisiae* using CRISPR-Cas systems," Nucleic Acids Research, (2013) vol. 41, No. 7: 4336-4343.
Xu, et al., "Efficient genome engineering in eukaryotes using Cas9 from *Streptococcus thermophilus*," Cell. Mol. Life Sci., (2015) vol. 72: 383-399.
Cencic, et al., "Protospacer Adjacent Motif (PAM)-Distal Sequences Engage CRISPR Cas9 DNA Target Cleavage," Plos One, (2014) vol. 9, Issue 10: 1-13.
Ryan, et al., "Selection of chromosomal DNA libraries using a multiplex CRISPR system," eLife (2014), vol. 3:e03703.
Vernis, et al., "Only Centromeres Can Supply the Partition System Required for ARS Function in the Yeast *Yarrowia lipolybca*," J. Mol. Biol., (2013) vol. 305: 203-217.
Gao, et al., "Self-processing of ribozyme-flanked RNAs into guide RNAs in vitro and in vivo for CRISPR-mediated genome editing," Journal of Integrative Plant Biology, (2014) vol. 56, Issue 4: 343-349.
Sakai, et al., "High-Frequency Transformation of a Methylotrophic Yeast, *Candida boidinii*, with Autonomously Replicating Plasmids Which Are Also Functional in *Saccharomyces cerevisiae*," Journal of Bacteriology, (1993) vol. 175, No. 31: 3556-3562, No. 11.

* cited by examiner

*Primary Examiner* — Gary B Nickol
*Assistant Examiner* — Lakia J Jackson-Tongue
(74) *Attorney, Agent, or Firm* — McBee Moore & Vanik IP, LLC

(57) ABSTRACT

The present invention relates to the field of molecular biology and cell biology. More specifically, the present invention relates to a CRISPR-CAS system for a lipolytic yeast host cell.

19 Claims, 5 Drawing Sheets
Specification includes a Sequence Listing.

Fig. 3

→ = strain with brown phenotype    ⇢ = growth on MM-agar -> no mutation

Fig. 5

CRISPR-CAS SYSTEM FOR A LIPOLYTIC YEAST HOST CELL

CROSS-REFERENCE TO RELATED APPLICATIONS

This application is a National Stage entry of International Application No. PCT/EP2016/050135 filed 6 Jan. 2016, which claims priority to European Patent Application No. 15150135.0, filed 6 Jan. 2015, European Patent Application No. 15150148.3, filed 6 Jan. 2015, and U.S. Patent Application No. 62/177497, filed 16 Mar. 2015.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2919208-313002_ST25.txt" created on 14 Jun. 2017, and 26,777,693 bytes in size) is submitted concurrently with the instant application, and the entire contents of the Sequence Listing are incorporated herein by reference.

FIELD OF THE INVENTION

The present invention relates to the field of molecular biology and cell biology. More specifically, the present invention relates to a CRISPR-CAS system for a lipolytic yeast host cell.

BACKGROUND TO THE INVENTION

Recent advances in genomics techniques and analysis methods have significantly accelerated the ability to e.g. catalog and map genetic factors associated with a diverse range of biological functions and diseases. Precise genome engineering technologies are needed to enable systematic reverse engineering of causal genetic variations by allowing selective perturbation of individual genetic elements, as well as to advance synthetic biology, biotechnological, and medical applications. Although genome-editing techniques such as designer zinc fingers, transcription activator-like effectors nucleases (TALENs), or homing meganucleases are available for producing targeted genome perturbations, there remains a need for new genome engineering technologies that are affordable, easy to set up, scalable, and amenable to targeting multiple positions within a genome. The engineering of meganucleases has been challenging for most academic researchers because the DNA recognition and cleavage functions of these enzymes are intertwined in a single domain. Robust construction of engineered zinc finger arrays has also proven to be difficult for many laboratories because of the need to account for context-dependent effects between individual finger domains in an array. There thus exists a pressing need for alternative and robust techniques for targeting of specific sequences within a host cell with a wide array of applications.

SUMMARY OF THE INVENTION

The present invention addresses above described need and provides such technique. The present invention is based on the CRISPR-Cas system, which does not require the generation of customized proteins to target-specific sequences but rather a single Cas enzyme that can be programmed by a guide-polynucleotide to recognize a specific polynucleotide target; in other words, the Cas enzyme can be recruited to a specific polynucleotide target using said guide-polynucleotide molecule. Adding the CRISPR-Cas system to the repertoire of genomics techniques and analysis methods may significantly simplify existing methodologies in the field of molecular biology.

The present invention provides a non-naturally occurring or engineered composition comprising a source of a CRISPR-Cas system comprising a guide-polynucleotide and a Cas protein, wherein the guide-polynucleotide comprises a sequence that essentially is the reverse complement of a target-polynucleotide in a host cell and the guide-polynucleotide can direct binding of the Cas protein at the target-polynucleotide in the host cell to form a CRISPR-Cas complex.

The present invention further relates to a method of modulating expression of a polynucleotide in a cell, comprising contacting a host cell with the composition according to the present invention, wherein the guide-polynucleotide directs binding of the Cas protein at the target-polynucleotide in the host cell to form a CRISPR-Cas complex.

The present invention further relates to a host cell comprising a composition according to the present invention.

The present invention further relates to a method of producing a host cell, comprising contacting a host cell with the composition according to the present invention, wherein the guide-polynucleotide directs binding of the Cas protein at the target-polynucleotide in the host cell to form a CRISPR-Cas complex.

The present invention further relates to a method for the production of a compound of interest, comprising culturing under conditions conducive to the compound of interest a host cell according to the present invention and optionally purifying or isolating the compound of interest.

BRIEF DESCRIPTION OF THE DRAWINGS

FIG. 3 depicts the results of example 10; sequencing of mutants obtained is shown in (SEQ ID NO: 92).

DESCRIPTION OF THE SEQUENCE LISTING

Figure 1:
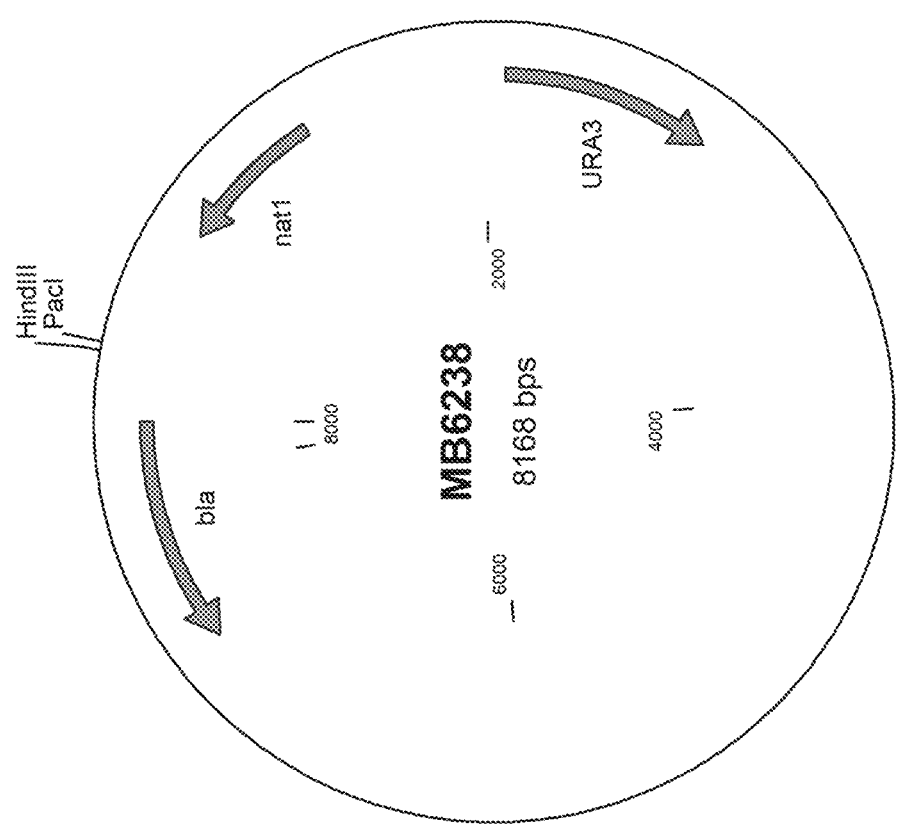
FIG. 1 depicts vector MB6238, containing a URA3 marker and CEN/ARS sequence for *S. cerevisiae, E. coli* ori and an Ampicillin resistance marker for *E. coli*.

SEQ ID NO: 1-3 empty.
SEQ ID NO: 4 sets out the genome of *Yarrowia lipolytica* CLIB122.
SEQ ID NO: 5-68 empty.
SEQ ID NO: 95-124 empty.
Sequences in examples 1-10
SEQ ID NO: 69 sets out the promoter fragment YI-PRO28 functional in *Yarrowia lipolytica*.
SEQ ID NO: 70 sets out the coding sequence of CAS9
SEQ ID NO: 71 sets out the terminator sequence YI-ter02
SEQ ID NO: 72 sets out the backbone vector 5a
SEQ ID NO: 73 sets out resulting vector BG-C1
SEQ ID NO: 74 sets out the promoter fragment YI-PRO07
SEQ ID NO: 75 sets out gRSR
SEQ ID NO: 76 sets out the terminator sequence YI-ter04
SEQ ID NO: 77 sets out the backbone vector ab
SEQ ID NO: 78 sets out resulting vector BG-C4

SEQ ID NO: 79 sets out forward primer DBC-12192
SEQ ID NO: 80 sets out reverse primer DBC-05794
SEQ ID NO: 81 sets out forward primer DBC-05795
SEQ ID NO: 82 sets out reverse primer DBC-12194
SEQ ID NO: 83 sets receiving vector MB6238
SEQ ID NO: 84 sets out the gBlock donor DNA
SEQ ID NO: 85 sets out forward primer gBlock DBC-12197
SEQ ID NO: 86 sets out reverse primer gBlock DBC-12198
SEQ ID NO: 87 sets out the Hygromycin marker cassette
SEQ ID NO: 88 sets out forward primer DBC-05799
SEQ ID NO: 89 sets out reverse primer DBC-05800
SEQ ID NO: 90 sets out forward primer in front ade33 DBC-12607
SEQ ID NO: 91 sets out the wild-type ADE33 sequence
SEQ ID NO: 92 sets out the mutated ADE33 sequence
SEQ ID NO: 93 sets out forward primer DBC-05793
SEQ ID NO: 94 sets out reverse primer DBC-05796

DETAILED DESCRIPTION OF A PREFERRED EMBODIMENT

In a first aspect, the present invention provides a non-naturally occurring or engineered composition comprising a source of a CRISPR-Cas system comprising a guide-polynucleotide and a Cas protein, wherein the guide-polynucleotide comprises a guide-sequence that essentially is the reverse complement of a target-polynucleotide in a host cell and the guide-polynucleotide can direct binding of the Cas protein at the target-polynucleotide in the host cell to form a CRISPR-Cas complex, wherein the guide-sequence is essentially the reverse complement of the (N)y part of a 5'-(N)yPAM-3' polynucleotide sequence target in the genome of the host cell, wherein y is an integer of 8-30, more preferably 10-30, more preferably 15-30, more preferably 17-27, more preferably 17-20, more preferably 17, 18, 19, 20, 21, 22, 23, 24, 25, 26, or 27, wherein PAM is a protospacer adjacent motif, wherein the host cell is a lipolytic yeast, preferably a *Yarrowia*, more preferably a *Yarrowia lipolytica*, even more preferably *Yarrowia lipolytica* CL1B122 or *Yarrowia lipolytica* ML324 (deposited under number ATCC18943), and wherein PAM is preferably a sequence selected from the group consisting of 5'-XGG-3', 5'-XGGXG-3', 5'-XXAGAAW-3', 5'-XXXX-GATT-3', 5'-XXAGAA-3', 5'-XAAAAC-3', wherein X can be any nucleotide or analog thereof, preferably X can be any nucleotide; and W is A or T.

A preferred genome of *Yarrowia* is the genome represented by SEQ ID NO: 4. Unknown or ambiguous nucleotides in a genome (such as a nucleotide depicted with "n") are preferably excluded as polynucleotide sequence target.

The composition, source, CRISPR-Cas system, guide-polynucleotide, Cas protein, target-polynucleotide, host cell and CRISPR-Cas complex are herein referred to as a composition, source, CRISPR-Cas system, guide-polynucleotide, Cas protein, target-polynucleotide, host cell and CRISPR-Cas complex according to the present invention. For the sake of completeness, since "a" is defined elsewhere herein as "at least one", a composition according to the present invention comprises a source of at least one, i.e. one, two, three or more guide-polynucleotides and/or at least one, i.e. one, two, three or more Cas proteins. Accordingly, the present invention conveniently provides for a multiplex CRISPR-Cas system. Such multiplex CRISPR-Cas system can conveniently be used for introduction of a donor polynucleotide, deletion of a polynucleotide and polynucleotide library insertion into the genome of a host cell. Herein, a multiplex CRISPR-Cas system may refer to the use of one of more Cas proteins, one of more guide-polynucleotides and/or one or more donor polynucleotides. Herein, when a combination of a single guide-polynucleotide and multiple donor polynucleotides is used wherein the donor polynucleotides are configured such that they will be introduced into a single target locus, the term "singleplex" is used.

The terms "CRISPR system", "CRISPR-Cas system" and "CRISPR enzyme system" are used interchangeably herein and refer in the context of all embodiments of the present invention to a collection of elements required to form, together with a target-polynucleotide, a CRISPR-Cas complex; these elements comprise but are not limited to a Cas protein and a guide-polynucleotide.

The term "CRISPR-Cas complex" refers in the context of all embodiments of the present invention to a complex comprising a guide-polynucleotide hybridized to a target-polynucleotide and complexed with a Cas protein. In the most straightforward form, where a non-mutated Cas protein is used such as but not limited to the Cas9 protein of *Streptococcus pyogenes*, the formation of the CRISPR-Cas complex results in cleavage of one or both polynucleotide strands in or near (e.g. within 1, 2, 3, 4, 5, 6, 7, 8, 9, 10, 20, 50, or more base pairs from) the target-polynucleotide. Typically, a target-polynucleotide according to the present invention (defined below herein) is associated with a PAM sequence (defined below herein) and the PAM sequence is preferably immediately downstream (3') of the target-polynucleotide; the formation of the CRISPR-Cas complex typically results in cleavage of one or both polynucleotide strands 3 base pairs upstream (5') of the PAM sequence.

The term "non-naturally occurring composition" refers in the context of all embodiments of the present invention to a composition that in its form used in the present invention does not occur in nature. The individual elements may e.g. occur as such or in combinations with other elements in nature, but the non-naturally occurring composition comprises e.g. at least one element more or less than a naturally composition.

The term "engineered composition" refers in the context of all embodiments of the present invention to a composition wherein at least one of the elements has been engineered, i.e. modified by man, in such a way that resulting element does not occur in nature. It follows that by virtue of comprising at least one engineered element, an engineered composition does not occur in nature.

The terms "polynucleotide", "nucleotide sequence" and "nucleic acid" are used interchangeably herein and refer in the context of all embodiments of the present invention to a polymeric form of nucleotides of any length, either deoxyribonucleotides or ribonucleotides, or mixes or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, oligonucleotides and primers. A polynucleotide may comprise one or more modified nucleotides, such as a methylated nucleotide and a nucleotide analogue or nucleotide equivalent wherein a nucleotide analogue or equivalent is defined as a residue having a modified base, and/or a modified backbone, and/or a non-natural internucleoside linkage, or a combination of these modifications. Preferred nucleotide analogues and equivalents are described in the section "General definitions". As desired, modifications to the nucleotide structure may be introduced before or after assembly of the polynucleotide. A polynucleotide may be further modified after polymerization, such as by conjugation with a labeling compound.

A guide-polynucleotide according to the present invention comprises at least a guide-sequence that is able to hybridize with the target-polynucleotide and is able to direct sequence-specific binding of the CRISPR-Cas system to the target-polynucleotide to form a CRISPR-Cas complex. In order to enable formation of an active CRISPR-Cas complex, the guide-polynucleotide preferably also comprises a sequence that has a specific secondary structure and allows binding of the Cas protein to the guide-polynucleotide. Such sequence is known in the art as tracrRNA, tracr sequence, tracr scaffold or guide-polynucleotide structural component, these terms are used interchangeably herein; wherein the tracr is the abbreviation for transactivating CRISPR; tracr-RNA thus means transactivating CRISPR RNA. The tracr-RNA in the original CRISPR-Cas system is the endogenous bacterial RNA that links the crRNA (guide-sequence) to the Cas nuclease, being able to bind any crRNA. A guide-polynucleotide structural component may be comprised of a single polynucleotide molecule or may be comprised of two or more molecules hybridized to each other; such hybridizing components of a guide-polynucleotide structural component may be referred to as a tracr sequence and a tracr-mate sequence.

Accordingly, the guide-polynucleotide preferably also comprises a tracr sequence and/or a tracr-mate sequence. The guide-polynucleotide is a polynucleotide according to the general definition of a polynucleotide set out here above; a preferred guide-polynucleotide comprises ribonucleotides, a more preferred guide-polynucleotide is a RNA (guide-RNA). Two examples of typical guide-polynucleotide structures are depicted in Sander and Joung, 2014.

In the context of the present invention, a sequence is referred to as essentially the reverse complement of a target-sequence or of a target-polynucleotide if the subject sequence is able to hybridize with the target-sequence or target-polynucleotide, preferably under physiological conditions as in a host cell. The degree of complementarity between a guide-sequence and its corresponding target-sequence, when optimally aligned using a suitable alignment algorithm, is preferably higher than 50%, 60%, 75%, 80%, 85%, 90%, 95%, 97.5%, 99% sequence identity. Optimal alignment may be determined using any suitable algorithm for aligning sequences, preferably an algorithm as defined herein under "Sequence identity". When the target-polynucleotide is a double stranded polynucleotide, the subject sequence, such as a guide-sequence, may be able to hybridize with either strand of the target-polynucleotide e.g. a coding strand or a non-coding strand.

Preferably, a guide-sequence according to the present invention targets a target-sequence that is unique in the target. Preferably, a guide-sequence according to the present invention has 100% sequence identity with the 8, 9, 10, 11, 12, 13, 14, 15, 16, 17, 18, 19 or 20, more preferably 8, 9, 10, 11 or 12 nucleotides in the target-polynucleotide immediately adjacent to a PAM sequence.

A guide-sequence according to the present invention preferably is 8-30, more preferably 10-30, more preferably 15-30, more preferably 17-27, more preferably 17-20, more preferably 17, 18, 19, 20, 21, 22, 23, 24, 25, 26, or 27 nucleotides in length. The ability of a guide-sequence to direct sequence-specific binding of a CRISPR-Cas system to a target-sequence to form a CRISPR-Cas complex may be assessed by any suitable assay. For example, the components of a CRISPR system sufficient to form a CRISPR-Cas complex, including the guide-sequence to be tested, may be provided to a host cell having the corresponding target-sequence, such, as by transfection with vectors encoding the components of the CRISPR-Cas system, followed by an assessment of preferential cleavage within the target-sequence, such as by the Surveyor assay (Surveyor® Mutation Detection Kits distributed by Integrated DNA Technologies, Leuven, Belgium) or another sequence analysis assay such as sequencing. Cleavage of a target-polynucleotide may be evaluated in a test tube by providing the target-polynucleotide, components of a CRISPR-Cas system, including the guide-sequence to be tested and a control guide-sequence different from the test guide-sequence, and comparing binding or rate of cleavage at the target-sequence between the test and control guide-sequence reactions. Other assays are possible, and are known to a person skilled in the art.

A guide-polynucleotide structural component is believed to be necessary for formation of an active CRISPR-Cas complex. The guide-polynucleotide structural component is believed not necessarily to be operably linked to the guide-sequence; however, a guide-polynucleotide structural component may be operably linked to a guide-sequence within a guide-polynucleotide. A guide-polynucleotide structural component according to the present invention, which may comprise or consist of all or a portion of a wild-type guide-polynucleotide structural component (e.g. about or more than about 20, 26, 32, 45, 48, 54, 63, 67, 85, or more nucleotides of a wild-type tracr-sequence) forms part of a CRISPR-Cas complex; e.g. by hybridization of at least a portion of a tracr-sequence according to the present invention to all or a portion of a tracr-mate sequence according to the present invention and preferably operably linked to a guide-sequence according to the present invention. A tracr-sequence according to the present invention has sufficient complementarity to a tracr-mate sequence according to the present invention to hybridize, preferably under physiological condition as in a host cell, and facilitate formation of a CRISPR-Cas complex. As with the target-sequence according to the present invention, it is believed that complete complementarity is not needed, provided there is sufficient complementarity to be functional. Preferably, the tracr-sequence according to the present invention has at least 50%, 60%, 70%, 80%, 90%, 95% or 99% sequence identity along the length of the tracr-mate sequence according to the present invention when optimally aligned. Optimal alignment may be determined using any suitable algorithm for aligning sequences, preferably an algorithm as defined herein under "Sequence identity".

In general, a tracr mate sequence according to the present invention includes any sequence that has sufficient complementarity with a tracr sequence according to the present invention to promote formation of a CRISPR-Cas complex at a target-sequence, wherein the CRISPR-Cas complex comprises the tracr mate sequence according to the present invention hybridized to the tracr sequence according to the present invention. The degree of complementarity of the tracr sequence according to the present invention and the tracr mate sequence according to the present invention is preferably defined with respect to optimal alignment of the tracr mate sequence and tracr sequence along the length of the shorter of the two sequences. Optimal alignment may be determined using any suitable algorithm for aligning sequences, preferably an algorithm as defined herein under "Sequence identity".

Preferably, with respect to a tracr mate sequence according to the present invention and a tracr sequence according to the present invention, secondary structures are taken into account, such as self-complementarity within either the tracr sequence or tracr mate sequence. Preferably, the degree of complementarity between the tracr sequence according to the present invention and tracr mate sequence according to the present invention along the length of the shorter of the two sequences when optimally aligned is higher than 50%, 60%, 75%, 80%, 85%, 90%, 95%, 97.5%, 99% sequence identity. Preferably, the tracr mate sequence according to the present invention is 5, 6, 7, 8, 9, 10, 11, 12, 13, 14, 15, 16, 17, 18, 19, 20, 25, 30, 40, 50, or more nucleotides in length. Preferably, the tracer sequence according to the present invention is 5, 6, 7, 8, 9, 10, 11, 12, 13, 14, 15, 16, 17, 18, 19, 20, 25, 30, 40, 50, or more nucleotides in length. Preferably, the tracr sequence according to the present invention and tracr mate sequence, i.e. the guide-polynucleotide structural component according to the present invention are comprised within a single transcript, such that hybridization between the two produces a hybridization complex comprising a secondary structure, such as a hairpin. Such hybridization complex may also be formed when the tracr sequence and the tracr mate sequence are not comprised in a single transcript. Preferred loop forming sequences in a tracr sequence according to the present invention and/or a tracr mate sequence according to the present invention and/or guide-polynucleotide structural component according to the present invention for formation of hairpin structures are four nucleotides in length, and most preferably have the sequence GAAA; longer or shorter loop sequences may be used, as may alternative sequences. The loop sequences preferably include a nucleotide triplet (for example, AAA), and an additional nucleotide (for example C or G). Examples of loop forming sequences include CAAA and AAAG. Preferably, a tracr sequence according to the present invention and/or tracr mate sequence according to the present invention or hybridization complex thereof and/or guide-polynucleotide structural component according to the present invention comprises or is able to form at least two or more hairpins. More preferably, a tracr sequence according to the present invention and/or tracr mate sequence according to the present invention or hybridization complex thereof and/or guide-polynucleotide structural component according to the present invention comprises or is able to form two, three, four or five hairpins. Preferably, a tracr sequence according to the present invention and/or tracr mate sequence according to the present invention or hybridization complex thereof and/or guide-polynucleotide structural component according to the present invention comprises or is able to form at most five hairpins. Preferably, the single transcript of a tracr sequence according to the present invention and a tracr-mate sequence according to the present invention or hybridization complex of a tracr sequence according to the present invention and a tracr mate sequence according to the present invention and/or guide-polynucleotide structural component according to the present invention further comprises a transcription termination sequence; preferably this is a polyT sequence, for example six T nucleotides. As said, guide-polynucleotide structural components are known to the person skilled in the art; background information can e.g. be found in Gaj et al, 2013.

In the context of all embodiments according to the present invention, the term "target-polynucleotide" refers to a target-sequence according to the present invention to which a guide-sequence according to the present invention is designed to have complementarity, where hybridization between a target-sequence according to the present invention and a guide-sequence according to the present invention promotes the formation of a CRISPR-Cas complex. Full complementarity is not necessarily required, provided there is sufficient complementarity to cause hybridization and promote formation of a CRISPR-Cas complex. Preferably, a guide-sequence according to the present invention targets a target-sequence that is unique in the target. Preferably, a guide-sequence according to the present invention has 100% sequence identity with the 8, 9, 10, 11, 12, 13, 14, 15, 16, 17, 18, 19 or 20, more preferably 8, 9, 10, 11 or 12 nucleotides in the target-polynucleotide immediately adjacent to a PAM sequence. A target-polynucleotide according to the present invention may comprise any polynucleotide, such as DNA or RNA polynucleotides and may be single or double stranded. When the target-polynucleotide is a double strand polynucleotide, a guide-sequence according to the present invention, may be able to hybridize with either strand of the target-polynucleotide e.g. a coding strand or a non-coding strand.

A target-polynucleotide according to the present invention may be located in the nucleus or cytoplasm of a cell. A target-polynucleotide according to the present invention may be located in an organelle of a host cell, for example in a mitochondrion or chloroplast. A target-polynucleotide according to the present invention may be comprised in a genome, may be comprised in a chromosome or may be extra-chromosomal, may be comprised in an artificial chromosome such a Yeast Artificial Chromosome (YAC), may be present in any chromosomal entity or extra-chromosomal entity such as an autosomal replicating entity such as an episomal plasmid or vector. A target-polynucleotide according to the present invention may be native or foreign to the host cell.

A target-polynucleotide according to the present invention is preferably associated with a protospacer adjacent motif (PAM), which is a short polynucleotide recognized by the CRISPR-Cas complex. Preferably, the target-polynucleotide and PAM are linked wherein the PAM is preferably immediately downstream (3') of the target-polynucleotide. The exact sequence and length of the PAM may vary, e.g. different Cas proteins may require different PAM's. A preferred PAM according to the present invention is a polynucleotide of 2 to 8 nucleotides in length. A preferred PAM is selected from the group consisting of 5'-XGG-3', 5'-XG-GXG-3', 5'-XXAGAAW-3', 5'-XXXXGATT-3', 5'-XX-AGAA-3', 5'-XAAAAC-3', wherein X can be any nucleotide or analog thereof, preferably any nucleotide; and W is A or T. A more preferred PAM is 5'-XGG-3'. The PAM is preferably matched with the Cas protein. The most widely used CAS/CRISPR system is derived from *S. pyogenes* and the matching PAM sequence 5'-XGG-3' is located immediately downstream (3') of the target-sequence. A preferred PAM for a *Neisseria meningitidis* Cas protein is 5'-XXXXGATT-3'; a preferred PAM for a *Streptococcus thermophilus* Cas protein is 5'-XXAGAA-3'; a preferred PAM for a *Treponema denticola* is 5'-XAAAAC-3'. A preferred PAM matches the Cas protein used. A Cas protein according to the present invention may be engineered to match a different PAM than the native PAM matching the wild-type Cas protein. As such, the CRISPR-Cas system according to the present invention may be used for customized specific targeting.

The term "hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence-specific manner. The complex may comprise two strands forming a duplex structure, three or more strands forming a multi stranded complex, a single self-hybridizing strand, or any combination of these. A hybridization reaction may constitute a step in a more extensive process, such as the cleavage of a polynucleotide by an enzyme. Preferred hybridization conditions are physiological conditions as within a host cell according to the present invention.

The term "source" in the context of all embodiments of the present invention refers to any source of a CRISPR-Cas system comprising a guide-polynucleotide and a Cas protein. The guide-polynucleotide and Cas protein may be present in separate sources. In such case, the composition according to the present invention comprises a CRISPR-Cas system comprising a source of a guide-polynucleotide and a source of a Cas-protein. Any source means that the guide-polynucleotide and Cas protein may be present as such in a form that they can function within a CRISPR-Cas system. The guide-polynucleotide and/or the Cas-protein may be provided in its active forms and may e.g. be provided from an inactive form or from another entity. The guide-polynucleotide may e.g. be present on another polynucleotide or may be encoded by a polynucleotide that is transcribed to provide for the actual guide-polynucleotide. The Cas protein may be encoded by a polynucleotide (e.g. DNA or mRNA) that is transcribed and/or translated to provide the actual Cas protein. An encoding polynucleotide may be present in a nucleic acid construct as defined herein and/or in a vector as defined herein. Such nucleic acid construct and vector are herein referred to as a nucleic acid construct according to the present invention and a vector according to the present invention.

Preferably, in the composition according to the present invention, the Cas protein is encoded by a polynucleotide and/or the guide-polynucleotide is encoded by or present on a polynucleotide.

Preferably, in the composition according to the present invention, the Cas protein is encoded by a polynucleotide and/or the guide-polynucleotide is encoded by or present on another polynucleotide and the polynucleotide or polynucleotides are comprised in a vector.

Preferably, in a composition according to the invention, the guide-polynucleotide is encoded by a polynucleotide that is transcribed to provide for the actual guide-polynucleotide. Accordingly, in an embodiment, in the composition according to the invention, preferably, the guide polynucleotide is present in the form of a polynucleotide encoding for said guide-polynucleotide and the guide-polynucleotide is obtained upon transcription of said polynucleotide in the host cell.

Preferably, in a composition according to the invention, the polynucleotide encoding a guide-polynucleotide has sequence identity with a vector such that recombination of the polynucleotide encoding the guide-polynucleotide and said vector is facilitated, wherein the recombination preferably is in vivo recombination in the host cell and wherein the vector is preferably linear. Accordingly, in an embodiment, in the composition according to the invention, preferably, a polynucleotide encoding a guide-polynucleotide has one or more regions of sequence identity with a first vector to allow homologous recombination between the polynucleotide encoding the guide-polynucleotide and said first vector to yield a second vector comprising the polynucleotide encoding the guide polynucleotide, wherein the recombination preferably is in vivo recombination in the host cell and wherein the first vector is preferably a linear vector. The person skilled in the art knows how to provide a linear vector; it can e.g. be synthesized as such or can be provided by restriction enzyme digestion of a circular vector. It allows the design of several distinct polynucleotides encoding a guide-polynucleotide that have homology with the vector without having to clone each polynucleotide encoding a guide-polynucleotide into the vector.

Preferably, such composition according to the invention comprises at least two distinct polynucleotides each encoding a respective distinct guide-polynucleotide, wherein said at least two polynucleotides additionally comprise sequence identity with each other such that recombination of the polynucleotides encoding the distinct guide-polynucleotides and said vector is facilitated, wherein the recombination preferably is in vivo recombination in the host cell and wherein the vector is preferably a linear vector. Accordingly, in an embodiment, the composition according to the invention preferably comprises at least two distinct polynucleotides each encoding a respective distinct guide-polynucleotide, wherein said at least two polynucleotides additionally comprise sequence identity with each other to allow homologous recombination of the polynucleotides encoding the distinct guide-polynucleotides with each other and with said (first) vector to yield a second vector comprising said at least two polynucleotides encoding each a guide-polynucleotide, wherein the recombination preferably is in vivo recombination in the host cell and wherein the (first) vector is preferably a linear vector. In an embodiment, the guide-polynucleotides are preferably distinct in their sequence identity with the target-polynucleotide.

In a variant embodiment, the polynucleotide encoding a guide-polynucleotide does not have sequence identity with a vector or another polynucleotide encoding a guide-polynucleotide itself, but an additional polynucleotide is present in the composition according to the invention that facilitates assembly of the polynucleotide encoding a guide-polynucleotide into the vector and/or assembly of a complex of two distinct polynucleotides each encoding a respective distinct guide-polynucleotide.

Accordingly, there is provided a composition according to the invention, wherein an additional set of polynucleotides is present that has sequence identity with a polynucleotide encoding a guide-polynucleotide and with a vector such that recombination of the polynucleotide encoding the guide-polynucleotide and said vector is facilitated, wherein the recombination preferably is in vivo recombination in the host cell and wherein the vector is preferably linear. In addition, there is provided a composition according to the invention, wherein a further polynucleotide is present that has sequence identity with a polynucleotide encoding the guide-polynucleotide and with a further and distinct polynucleotide encoding a further and distinct guide-polynucleotide such that recombination of the polynucleotides encoding the guide-polynucleotides and said vector is facilitated, wherein the recombination preferably is in vivo recombination in the host cell and wherein the vector is preferably linear.

Preferably, in the composition according to the present invention, the Cas protein is encoded by a polynucleotide and the guide-polynucleotide is encoded by or present on another polynucleotide and the polynucleotides are comprised in one vector.

Preferably, in the composition according to the present invention, the Cas protein is encoded by a polynucleotide comprised in a vector and the guide-polynucleotide is encoded by or present on another polynucleotide comprised in another vector. Preferably, the vector encoding the Cas protein is a low copy vector and the vector encoding the guide-polynucleotide is a high copy vector. This allows differential expression of the Cas protein and the guide-polynucleotide; the Cas protein may e.g. be expressed in lower level than the guide-polynucleotide. Preferably herein, a low copy vector is a vector that is present in an amount of at most 10, 9, 8, 7, 6, 5, 4, 3, 2 or most preferably 1 copy per host cell. Preferably herein, a high copy vector is a vector that is present in an amount of more than 10, at least 15, at least 20, 25, 30, 35, 40, 45, 50, 55, 60, 70, 80, 90, or at least 100 copies per host cell. Examples of low copy vectors are yeast replicating plasmids or yeast centromeric plasmids. An example of a high copy vector is a yeast episomal plasmid comprising the 2μ (also known as 2mu or 2 micron) origin of replication.

The invention thus provides for the possibilities that the guide-polynucleotide and the Cas protein are provided as such, or that they are encoded on or present on a vector. In the latter case, the encoding polynucleotides may each be on a separate vector or may both be on a single vector. The present invention, as depicted elsewhere herein, also provides for an exogenous polynucleotide, also referred to as a donor polynucleotide, a donor DNA when the polynucleotide is a DNA, or repair template, that upon cleavage of the target-polynucleotide by the CRISPR-Cas complex recombines with the target-polynucleotide, resulting in a modified target-polynucleotide. Such exogenous polynucleotide is herein referred to as an exogenous polynucleotide according to the present invention and may be single-stranded or double-stranded. Accordingly, a composition according to the present invention may further comprise an exogenous polynucleotide according to the present invention; a composition according to the invention may comprise one or more distinct exogenous polynucleotides. Such one or more distinct exogenous polynucleotides may encode different expression products or may encode identical expression products while a part of the exogenous polynucleotide has sequence identity to a part of the target-polynucleotide. In an embodiment, the composition according to the invention comprises one or more distinct exogenous polynucleotides, said exogenous polynucleotide comprise one or more regions of sequence identity to the target polynucleotide to allow, upon cleavage of the target-polynucleotide by the CRISPR-Cas complex, homologous recombination with the cleaved target-polynucleotide, resulting in a modified target-polynucleotide. Such compositions according to the invention allow for a multiplex CAS-CRISPR system according to the invention as referred to elsewhere herein. In an embodiment, in a composition according to the invention where at least two distinct exogenous polynucleotides are present that upon cleavage of the target-polynucleotide by the CRISPR-Cas complex recombine with the target-polynucleotides, resulting in a modified target-polynucleotide, said at least two distinct exogenous polynucleotides may comprise sequence identity with each other such that recombination of said distinct exogenous polynucleotides is facilitated, wherein the recombination preferably is in vivo recombination in the host cell. In an embodiment, the composition according to the invention comprising at least two distinct exogenous polynucleotides, each of said at least two distinct exogenous polynucleotides comprise at least one region of sequence identity with another exogenous polynucleotide and optionally with the target polynucleotide, to allow upon cleavage of the target-polynucleotide by the CRISPR-Cas complex, homologous recombination of said at least two distinct exogenous polynucleotides with one another and with the cleaved target-polynucleotide, resulting in a modified target-polynucleotide, wherein the recombination preferably is in vivo recombination in the host cell. Such compositions according to the invention allow for a singleplex CRISPR-Cas system according to the invention as described elsewhere herein. In a variant embodiment, an additional polynucleotide is present that has sequence identity with the exogenous and distinct polynucleotides such that recombination of the exogenous and distinct polynucleotides is facilitated, and wherein the recombination preferably is in vivo recombination in the host cell. In this variant embodiment, the additional polynucleotide or polynucleotides may have sequence identity with only the exogenous polynucleotides such that a complex of these can be formed. Alternatively, or in combination, an additional polynucleotide or polynucleotides may have sequence identity with an exogenous polynucleotide as well as sequence identity to a part of the target-polynucleotide such that the exogenous polynucleotide or complex of exogenous polynucleotides can be introduced into the target polynucleotide. The exogenous polynucleotide according to the present invention may be present on a vector or may be present as such, may be encoded by another polynucleotide or may be operably linked to the guide-polynucleotide and may have sequence identity to a part of the target-polynucleotide upstream of the PAM associated with the guide-sequence (i.e. on the 5' side of the PAM) or may have sequence identity to a part of the target-polynucleotide downstream of the PAM associated with the guide-sequence (i.e. on the 5' side of the PAM). The vector may be a separate vector for the exogenous polynucleotide. A vector carrying an exogenous polynucleotide may be any vector described herein below. The exogenous polynucleotide may be present on a vector that comprises a polynucleotide encoding a Cas protein according to the present invention and/or comprising a guide-polynucleotide or a polynucleotide encoding a guide-polynucleotide according to the present invention. Accordingly, in an embodiment, the present invention provides for a composition according to the present invention wherein a polynucleotide encoding a Cas protein according to the present invention, a guide-polynucleotide or a polynucleotide encoding a guide-polynucleotide according to the present invention are present on a single vector, which may further comprise any elements necessary for expressing the encoded products such as promoter and terminator elements. Such single (all-in-one) vector has the advantage that all components necessary for a CRISPR-Cas system are present together; in addition, a single transformation event, optionally in combination with a donor polynucleotide, suffices to introduce the components into a host cell. In an embodiment, there is provided a composition according to the present invention wherein a Cas protein according to the present invention is encoded by a polynucleotide which is present on a vector and a guide-polynucleotide according to the present invention is present as such (e.g. as a PCR fragment, a restriction fragment or a synthetic fragment), the guide-polynucleotide may be operably linked to an exogenous polynucleotide according to the present invention, wherein the guide-polynucleotide and/or the operably linked exogenous polynucleotide has sequence identity with the vector such that it allows in vivo recombination in the host cell of the guide-polynucleotide and/or the operably linked exogenous polynucleotide with the vector. Preferably, the in vivo recombination yields a second vector comprising the guide-polynucleotide and/or the operably linked exogenous polynucleotide. In case a guide-polynucleotide and an exogenous polynucleotide are operably linked and the guide-polynucleotide has sequence identity with the vector such as described here above, the exogenous polynucleotide is liberated when the guide-polynucleotide recombined with the vector. For the purposes described here above, the vector may be digested with a proper restriction enzyme (such as SapI) such that in vivo recombination is facilitated between the digested vector and the guide-polynucleotide and/or the operably linked exogenous polynucleotide. This embodiment enhances efficiency since it obviates the need for a vector-insert assembly step. These embodiments envisage that multiple distinct guide-polynucleotides can be used, or multiple distinct guide-polynucleotides operably linked to multiple distinct exogenous polynucleotides can be used, i.e. a library of guide-polynucleotides or guide-polynucleotides operably linked to multiple distinct exogenous polynucleotides. Such multiplex CRISPR-Cas system can conveniently be used for introduction of a donor polynucleotide sequence, deletion of a polynucleotide and polynucleotide library insertion into the genome of a host cell.

In the context of all embodiments of the present invention, a vector may be any vector (e.g., a plasmid or virus), which can conveniently be subjected to recombinant DNA procedures and can mediate expression of a polynucleotide according to the invention. The choice of the vector will typically depend on the compatibility of the vector with the host cell into which the vector is to be introduced. Preferred vectors are the vectors used in the examples herein. A vector may be a linear polynucleotide or a linear or closed circular plasmid. A vector may be an autonomously replicating vector, i.e., a vector, which exists as an extra-chromosomal entity, the replication of which is independent of chromosomal replication, e.g., a plasmid, an extra-chromosomal element, a mini-chromosome, or an artificial chromosome.

Preferably, in the composition according to the present invention, at least one vector is an autonomously replicating vector, preferably an AMA-vector. An autonomously maintained cloning vector and an AMA-vector preferably comprise the AMA1-sequence (see e.g. Aleksenko and Clutterbuck 1997) or a functional variant or equivalent thereof. A vector may be one which, when introduced into the host cell, becomes integrated into the genome and replicated together with the chromosome(s) into which it has been integrated. An integrative vector may integrate at random or at a predetermined target locus in a chromosome of the host cell. A preferred integrative vector comprises a DNA fragment, which is homologous to a DNA sequence in a predetermined target locus in the genome of the host cell for targeting the integration of the vector to this predetermined locus. In order to promote targeted integration, a vector is preferably linearized prior to transformation of the cell. Linearization is preferably performed such that at least one but preferably either end of the vector is flanked by sequences homologous to the target locus. The length of the homologous sequences flanking the target locus is preferably at least 30 bp, preferably at least 50 bp, preferably at least 0.1 kb, even preferably at least 0.2 kb, more preferably at least 0.5 kb, even more preferably at least 1 kb, most preferably at least 2 kb. Preferably, the efficiency of targeted integration into the genome of the host cell, i.e. integration in a predetermined target locus, is increased by augmented homologous recombination abilities of the host cell.

The homologous flanking DNA sequences in the vector (which are homologous to the target locus) may be derived from a highly expressed locus, meaning that they are derived from a gene, which is capable of high expression level in the host cell. A gene capable of high expression level, i.e. a highly expressed gene, is herein defined as a gene whose mRNA can make up at least 0.5% (w/w) of the total cellular mRNA, e.g. under induced conditions, or alternatively, a gene whose gene product can make up at least 1% (w/w) of the total cellular protein, or, in case of a secreted gene product, can be secreted to a level of at least 0.1 g/l (e.g. as described in EP 357 127 B1).

More than one copy of a polynucleotide according to the present invention may be inserted into the microbial host cell to mediate production of the product encoded by said polynucleotide. This can be done, preferably by integrating multiple copies of the polynucleotide into the genome of the host cell, more preferably by targeting the integration of the polynucleotide at one of the highly expressed loci defined in the former paragraph. Alternatively, integration of multiple copies can be achieved by including an amplifiable selectable marker gene with a polynucleotide according to the present invention, such that cells containing amplified copies of the selectable marker gene (and thereby additional copies of the nucleic acid sequence) can be selected for by cultivating the cells in the presence of the appropriate selectable agent. To increase the number of copies of a polynucleotide according the present invention even more, the technique of gene conversion as described in WO98/46772 may be used.

When a polynucleotide according to the present invention encoding a Cas protein according to the present invention and/or a guide-polynucleotide according to the present invention is integrated into the genome of the host cell, it may be desirable to excise the polynucleotide from the genome, e.g. when the desired genome editing has taken place. The excision of a polynucleotide can be performed by any means known to the person skilled in art; one preferred means is using Amds as a selection marker and counter-selecting with e.g. fluoroacetamide to excise the polynucleotide from the genome such as described in EP0635574. Another means for excision would be to use the well-known Cre/lox system; the polynucleotide sequence encoding the Cas-protein according to the present invention may e.g. be flanked by lox66/71 or loxP/loxP. A further means for excision would be to the use the CRISPR-Cas system according to the present invention. A vector according to the present invention may be a single vector or plasmid or a vector system comprising two or more vectors or plasmids, which together contain the polynucleotides according to the present invention to be introduced into the host cell host cell.

A vector according to the present invention may contain one or more selectable markers, which permit easy selection of transformed cells. In an embodiment, in a composition according to the invention, one or more or all vectors comprise a selectable marker, preferably each vector comprising a distinct selectable marker. A selectable marker is a gene the product of which provides for biocide or viral resistance, resistance to heavy metals, prototrophy to auxotrophs, and the like. The selectable marker may be introduced into the cell on the vector as an expression cassette or may be introduced on a separate vector.

A selectable marker for use in a fungal cell may be selected from the group including, but not limited to, amdS (acetamidase), argB (ornithine carbamoyltransferase), bar (phosphinothricinacetyltransferase), bleA (phleomycin binding), hygB (hygromycinphosphotransferase), niaD (nitrate reductase), pyrG (orotidine-5'-phosphate decarboxylase), sC (sulfate adenyltransferase), NAT or NTC (Nourseothricin) and trpC (anthranilate synthase), KanMX (resistance to G418/geneticin; the selection marker kanMX is a hybrid gene consisting of a bacterial aminoglycoside phosphotransferase (kanr from transposon Tn903) under control of the strong TEF promoter from *Ashbya gossypii*; mammalian cells, yeast, and other eukaryotes acquire resistance to geneticin (=G418, an aminoglycoside antibiotic similar to kanamycin) when transformed with a kanMX marker; in yeast, the kanMX marker avoids the requirement of auxotrophic markers; in addition, the kanMX marker renders *E. coli* resistant to kanamycin.) as well as equivalents from other species.

Markers which can be used in a prokaryotic host cell include ATP synthetase, subunit 9 (oliC), orotidine-5'-phosphatedecarboxylase (pvrA), the ampicillin resistance gene (*E. coli*), resistance genes for neomycin, kanamycin, tetracycline, spectinomycin, erythromycin, chloramphenicol, phleomycin (*Bacillus*) and the *E. coli* uidA gene, coding for β-glucuronidase (GUS). Vectors may be used in vitro, for example for the in vitro production of RNA in an in vitro transcription system or used to transfect or transform a host cell.

Versatile marker genes that can be used for transformation of most yeasts such as acetamidase genes or cDNAs (the amdS, niaD, facA genes or cDNAs from *A. nidulans, A. oryzae* or *A. niger*), or genes providing resistance to antibiotics like G418, hygromycin, bleomycin, kanamycin, methotrexate, phleomycin orbenomyl resistance (benA). Alternatively, specific selection markers can be used such as auxotrophic markers which require corresponding mutant host strains: e.g. D-alanine racemase (from *Bacillus*), URA3 (from *S. cerevisiae* or analogous genes from other yeasts), pyrG or pyrA (from *A. nidulans* or *A. niger*), argB (from *A. nidulans* or *A. niger*) or trpC. In a preferred embodiment the selection marker is deleted from the transformed host cell after introduction of the expression construct so as to obtain transformed host cells capable of producing the polypeptide which are free of selection marker genes.

The procedures used to ligate elements described above to construct a vector according to the present invention are well known to one skilled in the art (see, e.g. Sambrook & Russell, *Molecular Cloning: A Laboratory Manual*, 3rd Ed., CSHL Press, Cold Spring Harbor, N.Y., 2001; and Ausubel et al., *Current Protocols in Molecular Biology*, Wiley Inter-Science, NY, 1995).

A Cas protein in the context of all embodiments of the present invention refers to any Cas protein suitable for the purpose of the invention. A Cas protein may comprise enzymatic activity or may not comprise enzymatic activity. Non-limiting examples of Cas proteins include CasI, CasI B, Cas2, Cas3, Cas4, Cas5, Cas6, Cas7, Cas8, Cas9 (also known as CsnI and CsxI2), CasIO, CsyI, Csy2, Csy3, CseI, Cse2, CscI, Csc2, Csa5, Csn2, Csm2, Csm3, Csm4, Csm5, Csm6, CmrI, Cmr3, Cmr4, Cmr5, Cmr6, CsbI, Csb2, Csb3, CsxI7, CsxI4, CsxIO, CsxI6, CsaX, Csx3, CsxI, CsxIS, Cfl, Csf2, Csf3, Csf4, homologs thereof or modified versions thereof. These Cas proteins are known to the person skilled in the art; for example, the amino acid sequence of *S. pyogenes* Cas9 protein may be found in the SwissProt database under accession number Q99ZW2. Preferably, an unmodified Cas protein according to the present invention has DNA cleavage activity, such as e.g. Cas9. Preferably, a Cas protein according is Cas9, and may be Cas9 from *S. pyogenes* or *S. pneumoniae*. Preferably, a Cas protein according to the present invention directs cleavage of one or both polynucleotide strands at the location of the target-polynucleotide, such as within the target-polynucleotide and/or within the reverse complement of the target-polynucleotide. At the location of the target-polynucleotide is herein defined as within about 1, 2, 3, 4, 5, 6, 7, 8, 9, 10, 15, 20, 25, 50, 100, 200, 500, or more nucleotides from the first or last nucleotide of a target-polynucleotide; more preferably, within 1, 2, 3, 4, 5, 6, 7, 8, 9, 10, 15, 20, 25, 50, 100, 200, 500, or more nucleotides from the first or last nucleotide of a target-polynucleotide; even more preferably, within 1, 2, 3, 4, 5, 6, 7, 8, 9, 10, 15, 20, 25, 50 nucleotides from the first or last nucleotide of a target-polynucleotide. Accordingly, a Cas protein according to the present invention preferably directs cleavage of one or both polynucleotide strands within about 1, 2, 3, 4, 5, 6, 7, 8, 9, 10, 15, 20, 25, 50, 100, 200, 500, or more nucleotides from the first or last nucleotide of a target-polynucleotide; more preferably, within 1, 2, 3, 4, 5, 6, 7, 8, 9, 10, 15, 20, 25, 50, 100, 200, 500, or more nucleotides from the first or last nucleotide of a target-polynucleotide; even more preferably, within 1, 2, 3, 4, 5, 6, 7, 8, 9, 10, 15, 20, 25, 50 nucleotides from the first or last nucleotide of a target-polynucleotide. Typically, a target-polynucleotide according to the present invention is associated with a PAM sequence (defined elsewhere herein) and the PAM sequence is preferably immediately downstream (3') of the target-sequence; the formation of the CRISPR-Cas complex typically results in cleavage of one or both polynucleotide strands 3 base pairs upstream (5') of the PAM sequence. Preferably, a Cas protein in a composition according to the present invention has activity for directing cleavage of both polynucleotide strands at the location of the target-polynucleotide. Cas nuclease activity is typically performed by two separate catalytic domains, namely RuvC and HNH. Each domain cuts one polynucleotide strand each domain can be inactivated by a single point mutation. A Cas protein according to the present invention may thus conveniently be mutated with respect to a corresponding wild-type Cas protein such that the mutated Cas protein has altered nuclease activity and lacks the ability to cleave one or both strands of a target-polynucleotide. For example, an aspartate-to-alanine substitution (D10A) in the RuvC I catalytic domain of Cas9 from *S. pyogenes* converts Cas9 from a nuclease that cleaves both strands to a nickase, which is herein defined as a Cas protein that cleaves a single strand of a target-polynucleotide. Other examples of mutations that render Cas9 into a nickase include, but are not limited to H840A, N854A, and N863A. In the context of the present invention, a Cas protein having nickase activity may be used for genome editing via homologous recombination, preferably the double nicking technique according to Ran et al., 2013. Accordingly, a preferred Cas protein according to the present invention comprises at least one mutation, such that the protein has altered nuclease activity compared to the corresponding wild-type Cas protein, preferably having activity to direct cleavage of a single polynucleotide strand at the location of the target-sequence. Such so-called nickase mutant can conveniently be used in duplex set-up, i.e. in a composition according to the present invention comprising a Cas protein nickase mutant with RuvC mutated and a Cas protein nickase mutant wherein NHN is mutated, such that the one Cas protein mutant nicks one strand of the polynucleotide target and the other Cas protein mutant nicks the other strand of the polynucleotide target. Depending on the two guide-polynucleotides used, the two different CRISPR-Cas complexes will effectively result in two single-strand nicks in the polynucleotide target; these nicks may be several nucleotides up to 5, 10, 20, 30 or more apart. Such double nicking method greatly enhances specificity of NEJH. Background information on double nicking can be found in e.g. Ran et al, 2013.

A Cas protein according to the present invention may comprise two or more mutated catalytic domains of Cas9, such as RuvC I, RuvC II and/or RuvC III to result in a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. Preferably, a Cas protein is considered to substantially lack all DNA cleavage activity when the DNA cleavage activity of the mutated enzyme is less than about 25%, 10%, 5%, 1%, 0.1%, 0.01%, or lower with respect to its non-mutated form. A Cas protein lacking substantially all enzyme activity can conveniently be used for gene silencing or down regulation of expression since the CRISPR-CAS complex will hamper transcription from the target-polynucleotide. Other mutations may be useful; where the Cas9 or other Cas protein is from a species other than *S. pyogenes*, mutations in corresponding amino acids may be made to achieve similar effects; the person skilled in the art knows how to identify these corresponding amino acids.

A Cas protein according to the present invention may be a fusion protein and comprise at least one heterologous functional domain, such domain preferably is a domain comprising FokI activity such as described by Aggarwal et al (Aggarwal, A. K.; Wah, D. A.; Hirsch, J. A.; Dorner, L. F.; Schildkraut, I. (1997). "Structure of the multimodular endonuclease FokI bound to DNA". Nature 388 (6637): 97-100). The enzyme FokI is naturally found in *Flavobacterium okeanokoites* and is a bacterial type IIS restriction endonuclease consisting of an N-terminal DNA-binding domain and a non-specific DNA cleavage domain at the C-terminal (Durai et al., 2005). When the FokI protein is bound to double stranded DNA via its DNA-binding domain at the 5'-GGATG-3':3'-CATCC-5' recognition site, the DNA cleavage domain is activated and cleaves, without further sequence specificity, the first strand 9 nucleotides downstream and the second strand 13 nucleotides upstream of the nearest nucleotide of the recognition site (Wah et al., 1998. Cas9-FokI fusions have been described inter alia in Guilinger et al., 2014; and in Tsai et al., 2014.

A Cas fusion protein according to the present invention may comprise 1, 2, 3, 4, 5, 6, 7, 8, 9, 10, or more domains in addition to the Cas protein. Examples of protein domains that may be fused to a Cas protein include, but are not limited to, epitope tags, reporter gene sequences, and protein domains having one or more of the following activities: methylase activity, demethylase activity, transcription activation activity, transcription repression activity, transcription release factor activity, historic modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A Cas protein may be fused to a gene sequence encoding a protein or a fragment of a protein that bind DNA molecules or bind other cellular molecules, including but not limited to, maltose binding protein (MBP), S-tag, Lex A DNA binding domain (DBD) fusions, GAL4 DNA binding domain fusions, and herpes simplex virus (HSV) BP 16 protein fusions. Additional domains that may form part of a fusion protein comprising a CRISPR enzyme are described in US20110059502. A tagged Cas protein may be used to identify the location of a target-polynucleotide. A preferred Cas fusion protein according to the present invention comprises a FokI domain as defined here above.

A preferred Cas protein according to the present invention comprises a nuclear localization sequence, preferably a heterologous nuclear localization sequence. Such nuclear localization sequence is also referred as a nuclear localization signal. Preferably, such nuclear localization signal confers to the CRISPR-Cas complex sufficient strength to drive accumulation of said CRISPR-Cas complex in a detectable amount in the nucleus of a host cell. Without wishing to be bound by theory, it is believed that a nuclear localization sequence is not necessary for CRISPR-Cas activity in a host cell, but that including such sequences enhances activity of the system, especially as to targeting nucleic acid molecules into the nucleus. Such nuclear localization sequence is preferably present in the Cas protein, but may also be present anywhere else such that targeting of the CRISPR-Cas system to the nucleus is facilitated. A preferred nuclear localization sequence is the SV40 nuclear localization sequence.

In a composition and in any other embodiment according to the present invention a Cas protein encoding polynucleotide is preferably codon optimized for the host cell it is to be expressed in, more preferably the Cas protein encoding polynucleotide is codon pair optimized. In general, codon optimization refers to a process of modifying a nucleic acid sequence for enhanced expression in a host cell of interest by replacing at least one codon (e.g. more than 1, 2, 3, 4, 5, 10, 15, 20, 25, 50, or more codons) of a native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See e.g. Nakamura, Y., et al., 2000. Computer algorithms for codon optimizing a particular sequence for expression in a particular host cell are also available, such as Gene Forge (Aptagen; Jacobus, Pa.), are also available. Preferably, one or more codons (e.g. 1, 2, 3, 4, 5, 10, 15, 20, 25, 50, or more, or all codons) in a sequence encoding a Cas protein correspond to the most frequently used codon for a particular amino acid. Preferred methods for codon optimization are described in WO2006/077258 and WO2008/000632). WO2008/000632 addresses codon-pair optimization. Codon-pair optimization is a method wherein the nucleotide sequences encoding a polypeptide have been modified with respect to their codon-usage, in particular the codon-pairs that are used, to obtain improved expression of the nucleotide sequence encoding the polypeptide and/or improved production of the encoded polypeptide. Codon pairs are defined as a set of two subsequent triplets (codons) in a coding sequence. The amount of Cas protein in a source in a composition according to the present invention may vary and may be optimized for optimal performance. It may be convenient to avoid too high levels of Cas protein in a host cell since high levels of Cas protein may be toxic to the host cell, even without a guide-polynucleotide present (see e.g. Ryan et al 2014 and Jacobs et al., 2014). A person skilled in the art knows how to regulate expression levels, such as by choosing a weaker promoter, repressible promoter or inducible promoter for expression of a Cas protein. Examples of promoters suitable for expression of a protein are depicted elsewhere herein.

In a composition according to the present invention wherein a guide-polynucleotide according to the present invention is encoded by a polynucleotide, expression of the guide-polynucleotide may be facilitated by a promoter operably linked to the encoding polynucleotide. Such promoter may be any suitable promoter known to the person skilled in the art. Several types of promoters can be used. It may be convenient to use an RNA polymerase III promoter or an RNA polymerase II promoter. Background information on RNA polymerase III and its promoters can be found e.g. in Marck et al., 2006. In some cases, such as in *S. cerevisiae*, *S. pombe*, RNA polymerase III promoters include promoter elements in the transcribed region. Accordingly, it may be convenient to use an RNA polymerase II promoter; these are known to the person skilled in the art and reviewed in e.g. Kornberg 1999. However, transcripts from an RNA II polymerase often have complex transcription terminators and transcripts are polyadenylated; this may hamper with the requirements of the guide-polynucleotide which because both its 5' and 3' ends need to be precisely defined in order to achieve the required secondary structure to produce a functional CRISPR-Cas system. These drawbacks can however be circumvented. In case an RNA polymerase II promoter is used, the polynucleotide encoding the guide-polynucleotide may also encode self-processing ribozymes and may be operably linked to an RNA polymerase II promoter; as such the polynucleotide encodes a pre-guide-polynucleotide comprising the guide-polynucleotide and self-processing ribozymes, wherein, when transcribed, the guide-polynucleotide is released by the self-processing ribozymes from the pre-guide-polynucleotide transcript. Preferred constructs comprising a polynucleotide encoding a pre-guide-polynucleotide according to the present invention operably linked to an RNA polymerase II promoter are those depicted in examples 1-10 herein. Background information on such constructs can be found in e.g. Gao et al, 2014 et al.

Preferably, in a composition according to the present invention wherein the guide-polynucleotide is encoded by a polynucleotide, said polynucleotide is operably linked to an H1 RNA polymerase III promoter, preferably a human H1 RNA polymerase III promoter.

Preferably, in a composition according to the present invention wherein the guide-polynucleotide is encoded by a polynucleotide, said polynucleotide is operably linked to a U6 RNA polymerase III promoter, preferably a human U6 RNA polymerase III promoter.

Preferably, in a composition according to the present invention wherein the guide-polynucleotide is encoded by a polynucleotide, said polynucleotide is operably linked to an SNR52p RNA polymerase III promoter, preferably a yeast SNR52p RNA polymerase III promoter. Such promoter is preferably used when the host is a yeast host cell, such as a *Saccharomyces* or a *Kluyveromyces*.

Preferably, in a composition according to the present invention wherein the guide-polynucleotide is encoded by a polynucleotide, said polynucleotide is operably linked to an RNA polymerase II promoter and encodes a pre-guide-polynucleotide comprising the guide-polynucleotide and self-processing ribozymes, wherein, when transcribed, the guide-polynucleotide is released by the self-processing ribozymes from the pre-guide-polynucleotide transcript. Preferred constructs comprising a polynucleotide encoding a pre-guide-polynucleotide according to the present invention operably linked to an RNA polymerase II promoter are those depicted in examples 1-10 herein. Conveniently, multiple pre-guide-polynucleotides and multiple self-processing ribozymes may be encoded by a single polynucleotide, operably linked to one or more RNA polymerase II promoters.

The composition according to the first aspect of the present invention can conveniently be used to modulate expression of a polynucleotide in a host cell. Accordingly, in a second aspect, the present invention provides a method of modulating expression of a polynucleotide in a host cell, comprising contacting a host cell with the composition according to the first aspect of the invention, wherein the guide-polynucleotide directs binding of the Cas protein at the target-polynucleotide in the host cell to form a CRISPR-Cas complex.

The term "expression" in the context of the present invention is herein defined as the process by which a polynucleotide is transcribed from a polynucleotide template (e.g. a DNA template polynucleotide is transcribed into an mRNA polynucleotide transcript or other RNA transcript) and/or the process by which an mRNA transcript is subsequently translated into peptides, polypeptides, or proteins. Transcripts and encoded polypeptides may be collectively referred to as "gene product". If the polynucleotide transcript is derived from a genomic template DNA, expression may include splicing of the mRNA transcript in a host cell. The term "modulating expression" refers herein to increased or reduced expression compared to a parent host cell wherein expressing is not modulated when assayed using the same conditions. Reduced expression may be a reduced amount of transcript such as mRNA and/or a reduced amount of translation product such as a polypeptide. It follows that increased expression may be an enhanced amount of transcript such as mRNA and/or an enhanced amount of translation product such as a polypeptide.

Preferably, the CRISPR-Cas complex cleaves one or both polynucleotide strands at the location of the target-polynucleotide, resulting in modulated expression of the gene product. The CRISPR-Cas complex may also have altered nuclease activity and substantially lack the ability to cleave one or both strands of a target-polynucleotide; in such case, expression is modulated by the binding of the complex to the target-polynucleotide. A Cas protein lacking substantially all enzyme activity can conveniently be used for gene silencing or down regulation of expression since the CRISPR-Cas complex will hamper transcription from the target-polynucleotide. Alternatively, a Cas protein can be modified into a transcription factor for programmable transcriptional activation or silencing of a gene of interest (Larson, et al., 2013).

A composition according to the first aspect of the present invention can conveniently be used for the deletion of polynucleotide. In an embodiment, when the composition according to the first aspect of the present invention comprises a source of at least one or two guide-polynucleotides and/or a source of at least at least one Cas protein, at least one CRISPR-Cas complex or two different CRISPR-Cas complexes are formed that cleave one or both polynucleotide strands at one location or at different locations of the target-polynucleotide, resulting in deletion of a polynucleotide fragment from the target-polynucleotide. Preferably, such composition according to the present invention comprising at least one or two guide-polynucleotides and/or a source of at least at least one Cas protein, additionally comprises an exogenous polynucleotide as defined herein below that is at least partly complementary to the at least one or two target-polynucleotides targeted by the guide-polynucleotide(s). Such polynucleotide fragment to be deleted or deleted fragment may be several nucleotides in length up to a few thousand nucleotides in length, an entire gene may be deleted or a cluster of genes may be deleted. Accordingly, the present invention provides for a method of modulating expression of a polynucleotide in a host cell, wherein a polynucleotide fragment is deleted from a target-polynucleotide.

In an embodiment, the method of modulating expression comprises cleavage of one or both polynucleotide strands at least one location of the target-polynucleotide followed by modification of the target-polynucleotide by homologous recombination with an exogenous polynucleotide. In such case, the composition according to the first aspect of the present invention preferably further comprises such exogenous polynucleotide. Such modification may result in insertion, deletion or substitution of at least one nucleotide in the target-polynucleotide, wherein the insertion or substitution nucleotide may originate from the exogenous polynucleotide. A modification can also be made when the exogenous polynucleotide is a non-integrating entity such as described in Dong et al., and Beetham et al.; in this case the target-polynucleotide is modified but no nucleotide of the exogenous polynucleotide is introduced into the target-polynucleotide. Consequently, the resulting host is a non-recombinant host cell when the Cas-protein according to the invention is transformed as a protein. The exogenous polynucleotide may be any polynucleotide of interest such as a polynucleotide encoding a compound of interest as defined herein below, or a part of such polynucleotide or a variant thereof. Such exogenous polynucleotide is herein referred to as an exogenous polynucleotide according to the present invention and may single-stranded or double-stranded.

Various applications can be considered by the person skilled in the art for the compositions and methods according to the present invention. A polynucleotide (or gene) in a genome may be modified, edited or disrupted using compositions and methods according to the present invention. E.g. when a fully active Cas protein is used that cuts in both strands of the target-polynucleotide and when no exogenous polynucleotide is present as a suitable repair template, the double strand break is repaired by non-homologous end joining repair (NHEJ). During NHEJ insertions and/or deletions (which may be construed as substitution in some cases) of one or several nucleotides may occur, these are randomly inserted or deleted at the repair site; this is characteristic for NHEJ. Such insertions and/or deletions may impact the reading frame of the coding sequence, resulting amino acid changes in the gene product or even a truncated protein in case of genesis of a (premature) stop codon or alteration of a splice site.

A polynucleotide (or gene) in a genome may be modified, edited or disrupted using compositions and methods according to the present invention using homologous end joining repair (HEJ), also known as homology-directed repair (HDR), when an exogenous polynucleotide is present as repair template. E.g. when an exogenous polynucleotide having sequence identity to the target-polynucleotide (i.e. upstream (5') and downstream (3') of the double strand break) is present together with a CRISPR-Cas system according to the present invention, HDR will introduce (or actually reproduce) the corresponding nucleotides of the exogenous polynucleotide at the double strand break in the target-polynucleotide. Preferably, an exogenous polynucleotide according to the present invention does not contain the target sequence itself followed by a functional PAM sequence to avoid the risk of the exogenous polynucleotide itself or the modified target-polynucleotide being (re)cut by the CRISPR-CAS system.

In the embodiments of the present invention, when a CRISPR-Cas system according to the present invention comprises an exogenous polynucleotide (donor polynucleotide, donor DNA, repair template), the CRISPR-Cas system according to the present invention preferably comprises two or more guide-polynucleotides encoded by or present on one or more separate polynucleotides or vectors, and two or more exogenous polynucleotides are provided together with said CRISPR-Cas system enabling the formation of two or more CRISPR-CAS complexes. In a method according to the present invention, such CRISPR-Cas systems according to the present invention can conveniently be used to modulate expression at two or more target-polynucleotides, i.e. a method to target multiple target sites. Such CRISPR-Cas system according to the present invention will by chance form one, two or more CRISPR-CAS complexes at one or more target-polynucleotides. Such method can be used to generate one or more insertions, deletions, substitutions, optionally in combination with the one or more exogenous polynucleotides, in the genome of the host cell, or to modulate expression of genes via the formed CRISPR-CAS complexes.

In the embodiments of the present invention when a CRISPR-Cas system according to the present invention comprises an exogenous polynucleotide (donor polynucleotide, repair template), the exogenous polynucleotide and the guide-polynucleotide may be encoded by or present on a single polynucleotide. This enables synthesis of two or more of such combination polynucleotides and even library synthesis of such combination polynucleotides. Such library can be provided as a pool and be used to make a library of vectors and/or polynucleotides where the guide-polynucleotide and the exogenous polynucleotide are together encoded by or present on one polynucleotide. Such pool enables the use of a CRISPR-Cas system according to the present invention in a library-like multiplex system. In such CRISPR-Cas system according to the present invention, the exogenous polynucleotide and the guide-polynucleotide may be directly connected or may be separated by a linker polynucleotide.

In an embodiment, the guide-polynucleotide and the exogenous polynucleotide are connected by a linker polynucleotide that encodes for or represents the right flank of the guide-polynucleotide encoding or representing the gRNA 3' sequence and terminator, or a linker polynucleotide that encodes for or represents the left flank of the guide-polynucleotide encoding or representing the gRNA 5' sequence and promoter. This enables synthesis of two or more of such combination polynucleotides and even library synthesis of such combination polynucleotides. Such combination polynucleotides can be further processed to form a combination polynucleotide with one or more functional guide-polynucleotide(s) (containing a promoter and terminator).

In an embodiment, the guide-polynucleotide and the exogenous polynucleotide are connected by a linker polynucleotide that encodes for or represents the right flank of the guide-polynucleotide encoding or representing the gRNA 3' sequence and terminator and the polynucleotide target for said guide-polynucleotide, or a linker polynucleotide that encodes for or represents the polynucleotide target for said guide-polynucleotide and the left flank of the guide-polynucleotide encoding or representing the gRNA 5' sequence and promoter, where in vivo a CRISPR-Cas system can be formed at the combination polynucleotide to cleave the combination polynucleotide.

In an embodiment, one or more combination polynucleotides according to the present invention can be recombined (e.g. via direct cloning or in vivo recombination) with one or more vectors encoding Cas protein according to the present invention. One or more of such recombined vectors enable the formation of one or more CRISPR-CAS complexes. The host cell according to this aspect of the present invention may be any host cell as defined herein. A preferred host cell is a modified host cell wherein expression of a component associated with non-homologous end joining (NHEJ) is altered compared to the corresponding wild-type host cell; preferably expression of the component associated with NHEJ is lowered. Preferred components associated with NHEJ are the yeast Ku70 and Ku80 and their respective orthologs in preferred non-mammalian host cells according to the present invention. Another preferred component associated with NHEJ is the yeast LIG4 and its respective orthologs in preferred non-mammalian host cells according to the present invention.

In a method according to this aspect of the present invention, a preferred host cell comprises a polynucleotide encoding a compound of interest as defined elsewhere herein.

In a method according to this aspect of the present invention, the host cell may be a recombinant host cell or may be a non-recombinant host cell.

A method of modulating expression of a polynucleotide in a host cell according to this aspect of the present invention, results in a modified host cell that preferably comprises components of the composition according to the first aspect of the present invention. Accordingly, in a third aspect the present invention provides for a host cell comprising a composition according to the first aspect of the present invention. Such host cell may be any host cell as defined herein and may further comprise a polynucleotide encoding a compound of interest as defined elsewhere herein.

In a fourth aspect, the present invention provides a method of producing a host cell, comprising contacting a host cell with the composition according to the first aspect of the present invention, wherein the guide-polynucleotide directs binding of the Cas protein at the target-polynucleotide in the host cell to form a CRISPR-Cas complex. In an embodiment, the contacting with the composition according to the first aspect of the invention may be performed in two steps, wherein the host cell is first contacted with a source of a Cas protein according to the invention and subsequently the host cell is contacted with a source of a guide-polynucleotide according to the invention and optionally an exogenous polynucleotide according to the invention. A host cell in this embodiment of the present invention may be any type of host cell as defined herein and may comprise a polynucleotide encoding a compound of interest as defined elsewhere herein. A preferred method of producing a host cell according to the present invention comprises a step to produce an offspring host cell, wherein in said offspring host cell no components of a CRISPR-Cas system according to the present invention are present anymore. A further preferred host cell is a modified host cell wherein expression of a component associated with NHEJ as depicted here above is altered compared to the corresponding wild-type host cell; preferably expression of the component associated with NHEJ is lowered.

The composition according to the first aspect of the present invention may be any such composition as defined herein. Contacting a host cell with a composition according to the present invention may be performed by any means known to the person skilled in the art. A host cell according to the present invention may simply be brought into a solution comprising a composition according to the present invention. Specific means of delivering a composition according to the present invention into a host cell may be used. The person skilled in the art is aware of such methods (see e.g. Sambrook & Russell; Ausubel, supra)., which include but are not limited to electroporation methods, particle bombardment or microprojectile bombardment, protoplast methods and *Agrobacterium* mediated transformation (AMT). Yeast may be transformed using any method known in the art such as the procedures described by Becker and Guarente, In Abelson, J. N. and Simon, 1983; Hinnen et al., 1978, and Gietz R D, Woods R A. 2002.

Preferably, the CRISPR-Cas complex cleaves one or both polynucleotide strands at the location of the target-polynucleotide, resulting in modulated expression of the gene product. The CRISPR-Cas complex may also have altered nuclease activity and lack the ability to cleave one or both strands of a target-polynucleotide; in such case, expression is modulated by the binding of the complex to the target-polynucleotide.

In an embodiment, when the composition according to the first aspect of the present invention comprises a source of at least one or two guide-polynucleotides and/or a source of at least one Cas protein, at least one CRISPR-Cas complex or two different CRISPR-CAS complexes are formed that cleave one or both polynucleotide strands at one location or at different locations of the target-polynucleotide, resulting in deletion of a polynucleotide fragment from the target-polynucleotide. Preferably, such composition according to the present invention comprising at least one or two guide-polynucleotides and/or a source of at least at least one Cas protein, additionally comprises an exogenous polynucleotide as defined herein below that is at least partly complementary to the at least one or two target-polynucleotides targeted by the guide-polynucleotide(s). Such polynucleotide fragment to be deleted or deleted fragment may be from several nucleotides in length up to a few thousand nucleotides in length, an entire gene may be deleted or a cluster of genes may be deleted. Accordingly, the present invention provides for a method of modulating expression of a polynucleotide in a host cell, wherein a polynucleotide fragment is deleted from a target-polynucleotide.

In one embodiment a method of modulating expression of a polynucleotide in a host cell, wherein a polynucleotide fragments is deleted from a target-polynucleotide, comprises contacting a host cell with a composition as described herein, wherein the guide-polynucleotide directs binding of the Cas protein at the target-polynucleotide in the host cell to form a CRISPR-Cas complex. Preferably a method of modulating expression of a polynucleotide in a host cell, wherein a polynucleotide fragments is deleted from a target-polynucleotide, comprises contacting a host cell with a composition as described herein, wherein the guide-polynucleotide directs binding of the Cas protein at the target-polynucleotide in the host cell to form a CRISPR-Cas complex, wherein the host cell is a modified host cell deficient in a component associated with NHEJ. In another preferred embodiment a method of modulating expression of a polynucleotide in a host cell, wherein a polynucleotide fragments is deleted from a target-polynucleotide, comprises contacting a host cell with a composition as descried herein, wherein the guide-polynucleotide directs binding of the Cas protein at the target-polynucleotide in the host cell to form a CRISPR-Cas complex, wherein the host cell is a modified host cell deficient in a component associated with NHEJ, wherein the composition as described herein does not comprise an exogenous or donor polynucleotide. In one preferred embodiment the component associated with NHEJ is a yeast Ku70 or a yeast Ku80 or a yeast LIG4 or its respective ortholog in the host cells according to the present invention. In another embodiment of the method of modulating expression of a polynucleotide in a host cell the composition is comprised in an autonomously replicating vector.

Therefore the present invention relates in one embodiment to a method of modulating expression of a polynucleotide in a cell, wherein a polynucleotide fragment is deleted from a target-polynucleotide, comprising contacting a host cell with the composition as described herein but preferably not comprising a donor polynucleotide as defined herein, wherein the guide-polynucleotide directs binding of the Cas protein at the target-polynucleotide in the host cell to form a CRISPR-Cas complex, wherein the host cell is deficient in a component associated with NHEJ, preferably a yeast Ku70 or yeast Ku80 or a yeast LIG4 or its respective ortholog in the host cells.

Surprisingly it has been found that in a host cell deficient in a gene involved in NHEJ it is possible to obtain deletions in the host cell genome in a controlled way by using the CRISPR/CAS9 system when regions of homology are present at both sites of the intended cleavage site and wherein the composition as described herein does not comprise a donor DNA, in a method of modulating expression of a polynucleotide in a cell, wherein a polynucleotide fragment is deleted from a target-polynucleotide, as described herein.

Therefore in one embodiment the invention relates to a method of modulating expression of a polynucleotide in a cell, wherein a polynucleotide fragment is deleted from a target-polynucleotide, comprising contacting a host cell with a non-naturally occurring or engineered composition comprising a source of a CRISPR-Cas system comprising a guide-polynucleotide and a Cas protein, wherein the guide-polynucleotide comprises a guide-sequence that essentially is the reverse complement of a target-polynucleotide in a host cell and the guide-polynucleotide can direct binding of the Cas protein at the target-polynucleotide in the host cell to form a CRISPR-Cas complex, wherein the guide-sequence is essentially the reverse complement of the (N)y part of a 5'-(N)yPAM-3' polynucleotide sequence target in the genome of the host cell, wherein y is an integer of 8-30, wherein PAM is a protospacer adjacent motif, wherein the host cell is a lipolytic yeast, preferably a *Yarrowia*, more preferably a *Yarrowia lipolytica*, even more preferably *Yarrowia lipolytica* CL1B122 or *Yarrowia lipolytica* ML324 (deposited under number ATCC18943) and wherein PAM is preferably a sequence selected from the group consisting of 5'-XGG-3', 5'-XGGXG-3', 5'-XXAGAAW-3', 5'-XXXX-GATT-3', 5'-XXAGAA-3', 5'-XAAAAC-3', wherein X can be any nucleotide or analog thereof, preferably X can be any nucleotide; and W is A or T herein but preferably not comprising a donor polynucleotide as defined herein, wherein the guide-polynucleotide directs binding of the Cas protein at the target-polynucleotide in the host cell to form a CRISPR-Cas complex, wherein the host cell is deficient in a component associated with NHEJ, preferably a yeast Ku70 or yeast Ku80 or a yeast LIG4 or its respective ortholog in the host cells, wherein the Cas protein has activity for directing cleavage of both polynucleotide strands at the location of the target-sequence and wherein the cleavage occurs in a region of the genome comprised between two homologous regions which upon cleavage by the Cas protein recombine with each other resulting in the deletion of a polynucleotide comprised between said regions.

Preferably the degree of homology between the two homologous regions is such to allow homologous recombination. Preferably the two homologous regions have at least 60%, 70%, 80%, 90%, 99% or 100% sequence identity over the whole length of the homologous regions. It has been surprisingly found that the length of homologous region can be very short even in filamentous fungi, wherein usually a length of at least 1 or several kb is necessary to allow homologous recombination. Therefore in a preferred embodiment the length of the homologous regions is preferably at most 1 kb, at most 0.5 kb, at most 100 bp, at most 50 bp, at most 40 bp, at most 30 bp, at most 20 bp, at most 10 bp.

Preferably the distance between the two homologous regions is at most 10 kb, at most 9, at most 8 kb, at most 7 kb, at most 6 kb, at most 5 kb, at most 4 kb, at most 3 kb, at most 2 kb, at most 1 kb, at most 0.5 kb, at most 100 bp, at most 50 bp, at most 40 bp, at most 30, 20, 10 kb.

In one aspect, the invention relates to a software algorithms able to identify PAM sites in the genome comprised between homology regions of about 7-20 bp in a neighbourhood of the PAM site to design a method to target one or more PAM sites and create deletion of polynucleotides without use of a donor DNA.

The above method can be used for efficient removal of polynucleotide sequences in a designed way. For example upon introducing a Cas9 expression cassette at the genomic DNA and after several rounds of modifications mediated by the CRISPR/CAS9 system, one can remove the CAS9 from the genome by the introduction of a gRNA targeting a site in the Cas9 expression cassette and wherein the Cas9 expression cassette is comprised between two homologous regions as defined above, preferably 100-bp long, more preferably 20-bp, 15-bp long or shorter and cleave out the Cas9 open reading frame or a large part of the expression cassette.

The above method can also be used for transient inactivation of a gene. E.g. one could for example make a gene, e.g. a Ku70 polynucleotide non-functional by inserting a polynucleotide sequence in the ORF of the Ku70 gene, comprising two homologous regions at its 5'-end and 3'end respectively, wherein preferably the homologous regions are 100-bp, more preferably 20-bp, 15-bp long or shorter. The Ku70 gene can be made functional again using a CRISPR-Cas9 system without donor DNA as described above.

In an embodiment, the method of modulating expression comprises cleavage of one or both polynucleotide strands at least one location of the target-polynucleotide followed by modification of the target-polynucleotide by homologous recombination with an exogenous polynucleotide. In such case, the composition according to the first aspect of the present invention preferably further comprises such exogenous polynucleotide. Such modification may result in insertion, deletion or substitution of at least one nucleotide in the target-polynucleotide, wherein the insertion or substitution nucleotide may or may not originate from the exogenous polynucleotide. In one embodiment the exogenous polynucleotide comprises regions of homology with the target-polynucleotide. Preferably the degree of homology between these homologous regions is such to allow homologous recombination. Preferably the homologous regions have at least 60%, 70%, 80%, 90%, 99% or 100% sequence identity over the whole length of the homologous regions. In one embodiment, wherein the host cell is deficient in a component involve in NHEJ as defined herewith, the homologous regions are preferably at most 1 kb, at most 0.5 kb, at most 100 bp, at most 50 bp, at most 40 bp, at most 30 bp, at most 20 bp, at most 10 bp. A modification can also be made when the exogenous polynucleotide is a non-integrating entity; in this case the target-polynucleotide is modified but no nucleotide of the exogenous polynucleotide is introduced into the target-polynucleotide. Consequently, the resulting host is a non-recombinant host when the Cas-protein according to the present invention is transformed as a protein. In a method according to this aspect of the present invention, the host cell may thus be a recombinant host cell or may be a non-recombinant host cell. The exogenous polynucleotide may be any polynucleotide of interest such as a polynucleotide encoding a compound of interest as defined herein, or a part of such polynucleotide or a variant thereof.

In a fifth aspect, the present invention provides for a method for the production of a compound of interest, comprising culturing under conditions conducive to the compound of interest a host cell according to the third or fourth aspect of the present invention or a host cell obtained by a method according to the second aspect of the present invention, or a host cell obtainable by a method according to the fourth aspect of the present invention and optionally purifying or isolating the compound of interest.

A compound of interest in the context of all embodiments of the present invention may be any biological compound. The biological compound may be biomass or a biopolymer or a metabolite. The biological compound may be encoded by a single polynucleotide or a series of polynucleotides composing a biosynthetic or metabolic pathway or may be the direct result of the product of a single polynucleotide or products of a series of polynucleotides, the polynucleotide may be a gene, the series of polynucleotide may be a gene cluster. In all embodiments of the present invention, the single polynucleotide or series of polynucleotides encoding the biological compound of interest or the biosynthetic or metabolic pathway associated with the biological compound of interest, are preferred targets for the compositions and methods according to the present invention. The biological compound may be native to the host cell or heterologous to the host cell.

The term "heterologous biological compound" is defined herein as a biological compound which is not native to the cell; or a native biological compound in which structural modifications have been made to alter the native biological compound.

The term "biopolymer" is defined herein as a chain (or polymer) of identical, similar, or dissimilar subunits (monomers). The biopolymer may be any biopolymer. The biopolymer may for example be, but is not limited to, a nucleic acid, polyamine, polyol, polypeptide (or polyamide), or polysaccharide.

The biopolymer may be a polypeptide. The polypeptide may be any polypeptide having a biological activity of interest. The term "polypeptide" is not meant herein to refer to a specific length of the encoded product and, therefore, encompasses peptides, oligopeptides, and proteins. The term polypeptide refers to polymers of amino acids of any length. The polymer may he linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics. Polypeptides further include naturally occurring allelic and engineered variations of the above-mentioned polypeptides and hybrid polypeptides. The polypeptide may be native or may be heterologous to the host cell. The polypeptide may be a collagen or gelatine, or a variant or hybrid thereof. The polypeptide may be an antibody or parts thereof, an antigen, a clotting factor, an enzyme, a hormone or a hormone variant, a receptor or parts thereof, a regulatory protein, a structural protein, a reporter, or a transport protein, protein involved in secretion process, protein involved in folding process, chaperone, peptide amino acid transporter, glycosylation factor, transcription factor, synthetic peptide or oligopeptide, intracellular protein. The intracellular protein may be an enzyme such as, a protease, ceramidases, epoxide hydrolase, aminopeptidase, acylases, aldolase, hydroxylase, aminopeptidase, lipase. The polypeptide may also be an enzyme secreted extracellularly. Such enzymes may belong to the groups of oxidoreductase, transferase, hydrolase, lyase, isomerase, ligase, catalase, cellulase, chitinase, cutinase, deoxyribonuclease, dextranase, esterase. The enzyme may be a carbohydrase, e.g. cellulases such as endoglucanases, β-glucanases, cellobiohydrolases or β-glucosidases, hemicellulases or pectinolytic enzymes such as xylanases, xylosidases, mannanases, galactanases, galactosidases, pectin methyl esterases, pectin lyases, pectate lyases, endo polygalacturonases, exopolygalacturonases rhamnogalacturonases, arabanases, arabinofuranosidases, arabinoxylan hydrolases, galacturonases, lyases, or amylolytic enzymes; hydrolase, isomerase, or ligase, phosphatases such as phytases, esterases such as lipases, proteolytic enzymes, oxidoreductases such as oxidases, transferases, or isomerases. The enzyme may be a phytase. The enzyme may be an aminopeptidase, asparaginase, amylase, a maltogenic amylase, carbohydrase, carboxypeptidase, endo-protease, metallo-protease, serine-protease catalase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, protein deaminase, invertase, laccase, lipase, mannosidase, mutanase, oxidase, pectinolytic enzyme, peroxidase, phospholipase, galactolipase, chlorophyllase, polyphenoloxidase, ribonuclease, transglutaminase, or glucose oxidase, hexose oxidase, monooxygenase.

According to the present invention, a compound of interest can be a polypeptide or enzyme with improved secretion features as described in WO2010/102982. According to the present invention, a compound of interest can be a fused or hybrid polypeptide to which another polypeptide is fused at the N-terminus or the C-terminus of the polypeptide or fragment thereof. A fused polypeptide is produced by fusing a nucleic acid sequence (or a portion thereof) encoding one polypeptide to a nucleic acid sequence (or a portion thereof) encoding another polypeptide.

Techniques for producing fusion polypeptides are known in the art, and include, ligating the coding sequences encoding the polypeptides so that they are in frame and expression of the fused polypeptide is under control of the same promoter(s) and terminator. The hybrid polypeptides may comprise a combination of partial or complete polypeptide sequences obtained from at least two different polypeptides wherein one or more may be heterologous to the host cell. Example of fusion polypeptides and signal sequence fusions are for example as described in WO2010/121933.

The biopolymer may be a polysaccharide. The polysaccharide may be any polysaccharide, including, but not limited to, a mucopolysaccharide (e.g., heparin and hyaluronic acid) and nitrogen-containing polysaccharide (e.g., chitin). In a preferred option, the polysaccharide is hyaluronic acid.

A polynucleotide coding for the compound of interest or coding for a compound involved in the production of the compound of interest according to the invention may encode an enzyme involved in the synthesis of a primary or secondary metabolite, such as organic acids, carotenoids, (beta-lactam) antibiotics, and vitamins. Such metabolite may be considered as a biological compound according to the present invention.

The term "metabolite" encompasses both primary and secondary metabolites; the metabolite may be any metabolite. Preferred metabolites are citric acid, gluconic acid, adipic acid, fumaric acid, itaconic acid and succinic acid.

A metabolite may be encoded by one or more genes, such as in a biosynthetic or metabolic pathway. Primary metabolites are products of primary or general metabolism of a cell, which are concerned with energy metabolism, growth, and structure. Secondary metabolites are products of secondary metabolism (see, for example, R. B. Herbert, The Biosynthesis of Secondary Metabolites, Chapman and Hall, New York, 1981).

A primary metabolite may be, but is not limited to, an amino acid, fatty acid, nucleoside, nucleotide, sugar, triglyceride, or vitamin.

A secondary metabolite may be, but is not limited to, an alkaloid, coumarin, flavonoid, polyketide, quinine, steroid, peptide, or terpene. The secondary metabolite may be an antibiotic, antifeedant, attractant, bacteriocide, fungicide, hormone, insecticide, or rodenticide. Preferred antibiotics are cephalosporins and beta-lactams. Other preferred metabolites are exo-metabolites. Examples of exo-metabolites are Aurasperone B, Funalenone, Kotanin, Nigragillin, Orlandin, Other naphtho-γ-pyrones, Pyranonigrin A, Tensidol B, Fumonisin B2 and Ochratoxin A.

The biological compound may also be the product of a selectable marker. A selectable marker is a product of a polynucleotide of interest which product provides for biocide or viral resistance, resistance to heavy metals, protrophy to auxotrophs, and the like. Selectable markers include, but are not limited to, amdS (acetamidase), argB (ornithinecarbamoyltransferase), bar (phosphinothricinacetyltransferase), hygB (hygromycin phosphotransferase), niaD (nitrate reductase), pyrG (orotidine-5'-phosphate decarboxylase), sC (sulfate adenyltransferase), trpC (anthranilate synthase), ble (phleomycin resistance protein), hyg (hygromycin), NAT or NTC (Nourseothricin) as well as equivalents thereof.

According to the invention, a compound of interest is preferably a polypeptide as described in the list of compounds of interest.

According to another embodiment of the invention, a compound of interest is preferably a metabolite.

The host cell according to the present invention may already be capable of producing the compound of interest. The mutant microbial host cell may also be provided with a homologous or heterologous nucleic acid construct that encodes a polypeptide wherein the polypeptide may be the compound of interest or a polypeptide involved in the production of the compound of interest. The person skilled in the art knows how to modify a microbial host cell such that it is capable of producing the compound of interest General Definitions Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The terms "a" and "an" are used herein to refer to one or to more than one (i.e. to one or at least one) of the grammatical object of the article. By way of example, "an element" may mean one element or more than one element.

The word "about" or "approximately" when used in association with a numerical value (e.g. about 10) preferably means that the value may be the given value (of 10) more or less 1% of the value.

A preferred nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. It is further preferred that the linkage between a residue in a backbone does not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages.

A preferred nucleotide analogue or equivalent comprises a Peptide Nucleic Acid (PNA), having a modified polyamide backbone (Nielsen, et al. (1991) Science 254, 1497-1500). PNA-based molecules are true mimics of DNA molecules in terms of base-pair recognition. The backbone of the PNA is composed of N-(2-aminoethyl)-glycine units linked by peptide bonds, wherein the nucleobases are linked to the backbone by methylene carbonyl bonds. An alternative backbone comprises a one-carbon extended pyrrolidine PNA monomer (Govindaraju and Kumar (2005) Chem. Commun, 495-497). Since the backbone of a PNA molecule contains no charged phosphate groups, PNA-RNA hybrids are usually more stable than RNA-RNA or RNA-DNA hybrids, respectively (Egholm et al (1993) Nature 365, 566-568).

A further preferred backbone comprises a morpholino nucleotide analog or equivalent, in which the ribose or deoxyribose sugar is replaced by a 6-membered morpholino ring. A most preferred nucleotide analog or equivalent comprises a phosphorodiamidate morpholino oligomer (PMO), in which the ribose or deoxyribose sugar is replaced by a 6-membered morpholino ring, and the anionic phosphodiester linkage between adjacent morpholino rings is replaced by a non-ionic phosphorodiamidate linkage.

A further preferred nucleotide analogue or equivalent comprises a substitution of at least one of the non-bridging oxygens in the phosphodiester linkage. This modification slightly destabilizes base-pairing but adds significant resistance to nuclease degradation. A preferred nucleotide analogue or equivalent comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, selenophosphate or boranophosphate. A further preferred nucleotide analogue or equivalent comprises one or more sugar moieties that are mono- or disubstituted at the 2', 3' and/or 5' position such as a —OH; —F; substituted or unsubstituted, linear or branched lower (C1-C10) alkyl, alkenyl, alkynyl, alkaryl, allyl, aryl, or aralkyl, that may be interrupted by one or more heteroatoms; O—, S—, or N-alkyl; O—, S—, or N-alkenyl; O—, S—or N-alkynyl; O—, S—, or N-allyl; O-alkyl-O-alkyl, -methoxy, -aminopropoxy; aminoxy, methoxyethoxy; -dimethylaminooxyethoxy; and -dimethylaminoethoxyethoxy. The sugar moiety can be a pyranose or derivative thereof, or a deoxypyranose or derivative thereof, preferably a ribose or a derivative thereof, or deoxyribose or derivative thereof. Such preferred derivatized sugar moieties comprise Locked Nucleic Acid (LNA), in which the 2'-carbon atom is linked to the 3' or 4' carbon atom of the sugar ring thereby forming a bicyclic sugar moiety. A preferred LNA comprises 2'-O,4'-C-ethylene-bridged nucleic acid (Morita et al. 2001. Nucleic Acid Res Supplement No. 1: 241-242). These substitutions render the nucleotide analogue or equivalent RNase H and nuclease resistant and increase the affinity for the target.

"Sequence identity" or "identity" in the context of the present invention of an amino acid- or nucleic acid-sequence is herein defined as a relationship between two or more amino acid (peptide, polypeptide, or protein) sequences or two or more nucleic acid (nucleotide, oligonucleotide, polynucleotide) sequences, as determined by comparing the sequences. In the art, "identity" also means the degree of sequence relatedness between amino acid or nucleotide sequences, as the case may be, as determined by the match between strings of such sequences. Within the present invention, sequence identity with a particular sequence preferably means sequence identity over the entire length of said particular polypeptide or polynucleotide sequence.

"Similarity" between two amino acid sequences is determined by comparing the amino acid sequence and its conserved amino acid substitutes of one peptide or polypeptide to the sequence of a second peptide or polypeptide. In a preferred embodiment, identity or similarity is calculated over the whole sequence (SEQ ID NO:) as identified herein. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988). Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

A polynucleotide according to the present invention is represented by a nucleotide sequence. A polypeptide according to the present invention is represented by an amino acid sequence. A nucleic acid construct according to the present invention is defined as a polynucleotide which is isolated from a naturally occurring gene or which has been modified to contain segments of polynucleotides which are combined or juxtaposed in a manner which would not otherwise exist in nature. Optionally, a polynucleotide present in a nucleic acid construct according to the present invention is operably linked to one or more control sequences, which direct the production or expression of the encoded product in a host cell or in a cell-free system.

The sequence information as provided herein should not be so narrowly construed as to require inclusion of erroneously identified bases. The skilled person is capable of identifying such erroneously identified bases and knows how to correct for such errors.

All embodiments of the present invention, i.e. a composition according to the present invention, a method of modulating expression, a host cell comprising a composition according to the present invention, a method of producing a host cell according to the present invention, a host cell according to the present invention and a method for the production of a compound of interest according to the present invention preferably refer to host cell, not to a cell-free in vitro system; in other words, the CRISPR-Cas systems according to the present invention are preferably host cell systems, not cell-free in vitro systems.

In all embodiments of the present invention, e.g. a composition according to the present invention, a method of modulating expression, a host cell comprising a composition according to the present invention, a method of producing a host cell according to the present invention, a host cell according to the present invention and a method for the production of a compound of interest according to the present invention, the host cell may be a haploid, diploid or polyploid host cell.

The host cell according to the present invention is a lipolytic yeast host cell, preferably a *Yarrowia*, more preferably a *Yarrowia lipolytica*, even more preferably a *Yarrowia lipolytica* CLIB122 or a *Yarrowia lipolytica* ML324 (deposited as ATCC18943).

Preferably, a host cell according to the present invention further comprises one or more modifications in its genome such that the host cell is deficient in the production of at least one product selected from glucoamylase (glaA), acid stable alpha-amylase (amyA), neutral alpha-amylase (amyBI and amyBII), oxalic acid hydrolase (oahA), a toxin, preferably ochratoxin and/or fumonisin, a protease transcriptional regulator prtT, PepA, a product encoded by the gene hdfA and/or hdfB, a non-ribosomal peptide synthase npsE if compared to a parent host cell and measured under the same conditions.

Preferably, the efficiency of targeted integration of a polynucleotide to a pre-determined site into the genome of a host cell according to the invention is increased by rendering the cell deficient in a component in NHEJ (non-homologous recombination). Preferably, a host cell according to the invention comprises a polynucleotide encoding an NHEJ component comprising a modification, wherein said host cell is deficient in the production of said NHEJ component compared to a parent cell it originates from when cultivated under the same conditions.

The NHEJ component to be modified can be any NHEJ component known to the person skilled in the art. Preferred NHEJ components to be modified are selected from the group of homologues of yeast KU70, KU80, MRE11, RAD50, RAD51, RAD52, XRS2, SIR4, LIG4. A modification, preferably in the genome, is construed herein as one or more modifications. A modification, preferably in the genome of a host cell according to the present invention, can either be effected by a) subjecting a parent host cell to recombinant genetic manipulation techniques; and/or
b) subjecting a parent host cell to (classical) mutagenesis; and/or
c) subjecting a parent host cell to an inhibiting compound or composition. Modification of a genome of a host cell is herein defined as any event resulting in a change in a polynucleotide sequence in the genome of the host cell.

Preferably, a host cell according to the present invention has a modification, preferably in its genome which results in a reduced or no production of an undesired compound as defined herein if compared to the parent host cell that has not been modified, when analysed under the same conditions.

A modification can be introduced by any means known to the person skilled in the art, such as but not limited to classical strain improvement, random mutagenesis followed by selection. Modification can also be introduced by site-directed mutagenesis.

Modification may be accomplished by the introduction (insertion), substitution (replacement) or removal (deletion) of one or more nucleotides in a polynucleotide sequence. A full or partial deletion of a polynucleotide coding for an undesired compound such as a polypeptide may be achieved. An undesired compound may be any undesired compound listed elsewhere herein; it may also be a protein and/or enzyme in a biological pathway of the synthesis of an undesired compound such as a metabolite. Alternatively, a polynucleotide coding for said undesired compound may be partially or fully replaced with a polynucleotide sequence which does not code for said undesired compound or that codes for a partially or fully inactive form of said undesired compound. In another alternative, one or more nucleotides can be inserted into the polynucleotide encoding said undesired compound resulting in the disruption of said polynucleotide and consequent partial or full inactivation of said undesired compound encoded by the disrupted polynucleotide.

In one embodiment the mutant microbial host cell according to the invention comprises a modification in its genome selected from a) a full or partial deletion of a polynucleotide encoding an undesired compound,
b) a full or partial replacement of a polynucleotide encoding an undesired compound with a polynucleotide sequence which does not code for said undesired compound or that codes for a partially or fully inactive form of said undesired compound.
c) a disruption of a polynucleotide encoding an undesired compound by the insertion of one or more nucleotides in the polynucleotide sequence and consequent partial or full inactivation of said undesired compound by the disrupted polynucleotide.

This modification may for example be in a coding sequence or a regulatory element required for the transcription or translation of said undesired compound. For example, nucleotides may be inserted or removed so as to result in the introduction of a stop codon, the removal of a start codon or a change or a frame-shift of the open reading frame of a coding sequence. The modification of a coding sequence or a regulatory element thereof may be accomplished by site-directed or random mutagenesis, DNA shuffling methods, DNA reassembly methods, gene synthesis (see for example Young and Dong, (2004), *Nucleic Acids Research* 32, (7) electronic access http://nar.oupjournals.org/cgi/reprint/32/7/e59 or Gupta et al. (1968), *Proc. Natl. Acad. Sci USA*, 60: 1338-1344; Scarpulla et al. (1982), *Anal. Biochem.* 121: 356-365; Stemmer et al. (1995), *Gene* 164: 49-53), or PCR generated mutagenesis in accordance with methods known in the art. Examples of random mutagenesis procedures are well known in the art, such as for example chemical (NTG for example) mutagenesis or physical (UV for example) mutagenesis. Examples of site-directed mutagenesis procedures are the QuickChange™ site-directed mutagenesis kit (Stratagene Cloning Systems, La Jolla, Calif.), the 'The Altered Sites® II in vitro Mutagenesis Systems' (Promega Corporation) or by overlap extension using PCR as described in Gene. 1989 Apr. 15; 77(1):51-9. (Ho S N, Hunt H D, Horton R M, Pullen J K, Pease L R "Site-directed mutagenesis by overlap extension using the polymerase chain reaction") or using PCR as described in *Molecular Biology: Current Innovations and Future Trends*. (Eds. A. M. Griffin and H. G. Griffin. ISBN 1-898486-01-8; 1995 Horizon Scientific Press, PO Box 1, Wymondham, Norfolk, U.K.). Preferred methods of modification are based on recombinant genetic manipulation techniques such as partial or complete gene replacement or partial or complete gene deletion.

For example, in case of replacement of a polynucleotide, nucleic acid construct or expression cassette, an appropriate DNA sequence may be introduced at the target locus to be replaced. The appropriate DNA sequence is preferably present on a cloning vector. Preferred integrative cloning vectors comprise a DNA fragment, which is homologous to the polynucleotide and/or has homology to the polynucleotides flanking the locus to be replaced for targeting the integration of the cloning vector to this pre-determined locus. In order to promote targeted integration, the cloning vector is preferably linearized prior to transformation of the cell. Preferably, linearization is performed such that at least one but preferably either end of the cloning vector is flanked by sequences homologous to the DNA sequence (or flanking sequences) to be replaced. This process is called homologous recombination and this technique may also be used in order to achieve (partial) gene deletion.

For example a polynucleotide corresponding to the endogenous polynucleotide may be replaced by a defective polynucleotide, that is a polynucleotide that fails to produce a (fully functional) polypeptide. By homologous recombination, the defective polynucleotide replaces the endogenous polynucleotide. It may be desirable that the defective polynucleotide also encodes a marker, which may be used for selection of transformants in which the nucleic acid sequence has been modified.

Alternatively or in combination with other mentioned techniques, a technique based on in vivo recombination of cosmids in *E. coli* can be used, as described in: *A rapid method for efficient gene replacement in the filamentous fungus Aspergillus nidulans* (2000) Chaveroche, M-K., Ghico, J-M. and d'Enfert C; Nucleic acids Research, vol 28, no 22. Alternatively, modification, wherein said host cell produces less of or no protein such as the polypeptide having amylase activity, preferably α-amylase activity as described herein and encoded by a polynucleotide as described herein, may be performed by established anti-sense techniques using a nucleotide sequence complementary to the nucleic acid sequence of the polynucleotide. More specifically, expression of the polynucleotide by a host cell may be reduced or eliminated by introducing a nucleotide sequence complementary to the nucleic acid sequence of the polynucleotide, which may be transcribed in the cell and is capable of hybridizing to the mRNA produced in the cell. Under conditions allowing the complementary anti-sense nucleotide sequence to hybridize to the mRNA, the amount of protein translated is thus reduced or eliminated. An example of expressing an antisense-RNA is shown in Appl. Environ. Microbiol. 2000 February; 66(2):775-82. (*Characterization of a foldase, protein disulfide isomerase A, in the protein secretory pathway of Aspergillus niger. Ngiam C, Jeenes D J, Punt P J, Van Den Hondel C A, Archer D B*) or (Zrenner R, Willmitzer L, Sonnewald U. *Analysis of the expression of potato uridinediphosphate-glucose pyrophosphorylase and its inhibition by antisense RNA. Planta.* (1993); 190(2):247-52.).

A modification resulting in reduced or no production of undesired compound is preferably due to a reduced production of the mRNA encoding said undesired compound if compared with a parent microbial host cell which has not been modified and when measured under the same conditions.

A modification which results in a reduced amount of the mRNA transcribed from the polynucleotide encoding the undesired compound may be obtained via the RNA interference (RNAi) technique (Mouyna et al., 2004). In this method identical sense and antisense parts of the nucleotide sequence, which expression is to be affected, are cloned behind each other with a nucleotide spacer in between, and inserted into an expression vector. After such a molecule is transcribed, formation of small nucleotide fragments will lead to a targeted degradation of the mRNA, which is to be affected. The elimination of the specific mRNA can be to various extents. The RNA interference techniques described in WO2008/053019, WO2005/05672A1, WO2005/026356A1, Oliveira et al.; Crook et al., 2014; and/or Barnes et al., may be used at this purpose.

A modification which results in decreased or no production of an undesired compound can be obtained by different methods, for example by an antibody directed against such undesired compound or a chemical inhibitor or a protein inhibitor or a physical inhibitor (Tour O. et al, (2003) Nat. Biotech: Genetically targeted chromophore-assisted light inactivation. Vol. 21. no. 12:1505-1508) or peptide inhibitor or an anti-sense molecule or RNAi molecule (R. S. Kamath et al, (2003) Nature: Systematic functional analysis of the *Caenorhabditis elegans* genome using RNAi.vol. 421, 231-237).

In addition of the above-mentioned techniques or as an alternative, it is also possible to inhibiting the activity of an undesired compound, or to re-localize the undesired compound such as a protein by means of alternative signal sequences (Ramon de Lucas, J., Martinez O, Perez P., Isabel Lopez, M., Valenciano, S. and Laborda, F. The *Aspergillus nidulans* carnitine carrier encoded by the acuH gene is exclusively located in the mitochondria. FEMS Microbiol Lett. 2001 Jul. 24; 201(2):193-8.) or retention signals (Derkx, P. M. and Madrid, S. M. The foldase CYPB is a component of the secretory pathway of *Aspergillus niger* and contains the endoplasmic reticulum retention signal HEEL. Mol. Genet. Genomics. 2001 December; 266(4): 537-545), or by targeting an undesired compound such as a polypeptide to a peroxisome which is capable of fusing with a membrane-structure of the cell involved in the secretory pathway of the cell, leading to secretion outside the cell of the polypeptide (e.g. as described in WO2006/040340). Alternatively or in combination with above-mentioned techniques, decreased or no production of an undesired compound can also be obtained, e.g. by UV or chemical mutagenesis (Mattern, I. E., van Noort J. M., van den Berg, P., Archer, D. B., Roberts, I. N. and van den Hondel, C. A., Isolation and characterization of mutants of *Aspergillus niger* deficient in extracellular proteases. Mol Gen Genet. 1992 August; 234(2):332-6.) or by the use of inhibitors inhibiting enzymatic activity of an undesired polypeptide as described herein (e.g. nojirimycin, which function as inhibitor for β-glucosidases (Carrel F. L. Y. and Canevascini G. *Canadian Journal of Microbiology* (1991) 37(6): 459-464; Reese E. T., Parrish F. W. and Ettlinger M. *Carbohydrate Research* (1971) 381-388)).

In an embodiment of the present invention, the modification in the genome of the host cell according to the invention is a modification in at least one position of a polynucleotide encoding an undesired compound.

A deficiency of a cell in the production of a compound, for example of an undesired compound such as an undesired polypeptide and/or enzyme is herein defined as a mutant microbial host cell which has been modified, preferably in its genome, to result in a phenotypic feature wherein the cell: a) produces less of the undesired compound or produces substantially none of the undesired compound and/or b) produces the undesired compound having a decreased activity or decreased specific activity or the undesired compound having no activity or no specific activity and combinations of one or more of these possibilities as compared to the parent host cell that has not been modified, when analysed under the same conditions.

Preferably, a modified host cell according to the present invention produces 1% less of the un-desired compound if compared with the parent host cell which has not been modified and measured under the same conditions, at least 5% less of the un-desired compound, at least 10% less of the un-desired compound, at least 20% less of the un-desired compound, at least 30% less of the un-desired compound, at least 40% less of the un-desired compound, at least 50% less of the un-desired compound, at least 60% less of the un-desired compound, at least 70% less of the un-desired compound, at least 80% less of the un-desired compound, at least 90% less of the un-desired compound, at least 91% less of the un-desired compound, at least 92% less of the un-desired compound, at least 93% less of the un-desired compound, at least 94% less of the un-desired compound, at least 95% less of the un-desired compound, at least 96% less of the un-desired compound, at least 97% less of the un-desired compound, at least 98% less of the un-desired compound, at least 99% less of the un-desired compound, at least 99.9% less of the un-desired compound, or most preferably 100% less of the un-desired compound.

A reference herein to a patent document or other matter which is given as prior art is not to be taken as an admission that that document or matter was known or that the information it contains was part of the common general knowledge as at the priority date of any of the claims.

The sequence information as provided herein should not be so narrowly construed as to require inclusion of erroneously identified bases. The skilled person is capable of identifying such erroneously identified bases and knows how to correct for such errors. The disclosure of each reference set forth herein is incorporated herein by reference in its entirety.

The present invention is further illustrated by the following examples:

EXAMPLES

A Functional and Efficient CRISPR/CAS9 System in *Yarrowia lipolytica*

General Principle of the CRISPR/CAS9 System in *Yarrowia lipolytica*

Since the first publications and patents on CRISPR/CAS9 appeared (Mali et al., 2013), the wide spread use of this breakthrough technique has grown exponentially (Hsu et al., 2014). The use of CRISPR/CAS9 to create genomic modifications in human cell lines dominates the publications which can be easily explained by the possible medical applications of the technique. Use of CRISPR/CAS9 methods in other hosts are less abundant and for *Yarrowia* not shown. This example describes the set up and use of an efficient functioning CRISPR/CAS9 system for *Yarrowia* which uses guide RNA flanked by self-processing ribozymes, one step golden gate cloning techniques and a specifically adapted *Yarrowia* Cen ARS vector that makes it suitable for low and high throughput genome modifications. The structure and function of the guide RNA self-processing ribozymes abbreviated as gRSR in the examples is depicted in Gao and Zhao, 2014 which shows formation of the functional in vivo guide RNA.

Examples 1 to 10 describe the experiments demonstrating the functionality of CRISPR/CAS9 in *Y. lipolytica* using CAS9 in combination with a guide-RNA flanked by self-processing ribozymes abbreviated as gRSR in the examples. The functional guide-RNA is formed in vivo after the self-catalytic activity of the ribozymes have removed the 5' and 3' RNA sequences. In this specific example, a stop codon is introduced into a gene involved in the adenine pathway resulting in a auxotrophic strain not able to grow on minimal media.

Strain Used

ML324: This *Yarrowia lipolytica* strain is used as wild-type strain. This strain is deposited at ATCC under the deposit number ATCC18943.

CEN.PK113-13D: *Saccharomyces cerevisiae* (Δura3, MATa MAL2-8c SUC2)

Example 1

Assembly of the CAS9 Expression Cassette

The CAS9 expression cassette was constructed using the Golden Gate cloning method for combining promoter, open reading frame and terminator sequences described as step 1 in patent application WO2013/144257, which is herein incorporated by reference. Three fragments were synthesized at DNA2.0 and delivered in a standard cloning vector. First fragment is a promoter fragment YI-PRO28 functional in *Yarrowia lipolytica* (SEQ ID NO: 69). Second fragment is an open reading frame encoding the CAS9 protein (SEQ ID NO: 70). Third fragment is a *Y. lipolytica* terminator sequence YI-ter02 (SEQ ID NO: 71). The three separate DNA fragments were cloned by a Golden Gate reaction into the receiving backbone vector 5a (SEQ ID NO: 72). This resulted in the vector named BG-C1 (SEQ ID NO: 73) which contains the functional expression cassette for CAS9. The BG-C1 vector was checked using restriction enzyme analysis and used in the following examples.

Example 2

Assembly of the Guide-RNA Self-processing Ribozymes (gRSR) Expression Cassette with *Yarrowia* ADE33 as Genomic Target The gRSR expression cassette was constructed using the Golden Gate cloning method for combining promoter, open reading frame and terminator sequences described as step 1 in patent application WO2013/144257. Three fragments were synthesized at DNA2.0 and delivered in a standard cloning vector. First fragment is a promoter fragment functional in *Yarrowia lipolytica* YI_PRO07 (SEQ ID NO: 74). Second fragment is a DNA fragment with the sequence for the gRSR (SEQ ID NO: 75). Gao and Zhao 2014 describes how this fragment is build up. Third fragment is a *Y. lipolytica* terminator sequence YI_ter04 (SEQ ID NO: 76). The three separate DNA fragments were cloned with a Golden Gate reaction into backbone vector ab (SEQ ID NO: 77). The correct resulting vector named BG-C4 (SEQ ID NO: 78) was checked using restriction enzyme analysis and used in the following examples.

Example 3

PCR Amplification of Cassettes and Linearization of the Receiving Yeast/*E. coli* Shuttle Vector In vivo homologous recombination in *S. cerevisiae* was used to combine the gRSR cassette and CAS9 cassette into one fragment in the Yeast/*E. coli* shuttle vector. PCRs to create fragments with homology were done using Phusion polymerase (New England Biolabs) according to standard protocols. The CAS9 expression cassette was PCR amplified using forward primer DBC-12192 (SEQ ID NO: 79) and reverse primer DBC-05794 (SEQ ID NO: 80) and BG-C1 as a template. The gRSR expression cassette was PCR amplified using forward primer DBC-05795 (SEQ ID NO: 81) and reverse primer DBC-12194 (SEQ ID NO: 82) using BG-C4 as a template. The resulting PCR fragments contain the necessary homology to each other and to the receiving vector MB6238 (SEQ ID NO: 83, FIG. 1). Vector MB6238, containing a URA3 marker and CEN/ARS sequence for *S. cerevisiae*, *E. coli* ori and an Ampicillin resistance marker for *E. coli* was cut open with PacI and HindIII. All fragments, the PCR fragments and the cut-open vector, were purified with the PCR purification kit from Macherey Nagel used according to the manual. DNA concentration was measured using the NanoDrop (ND-1000 Spectrophotometer, Thermo Scientific).

Example 4

Transformation to *S. cerevisiae* CEN.PK113-13D Assembling the Fragments

Transformation of *S. cerevisiae* was essentially performed according to Gietz and Woods (2002; Transformation of the yeast by the LiAc/SS carrier DNA/PEG method. Methods in Enzymology 350: 87-96).

CenPK113-13d (Δura3, MATa MAL2-8c SUC2) was transformed with the vector MB6238 cut open with PacI and HindIII and both amplified and purified PCR fragments of the CAS9 expression cassette and gRSR expression cassette. Transformation mixtures were plated on YNB w/o AA plates (6.7 g/l YNB Difco, BD Becton Dickinson and Company, 20 g/l glucose, 20 g/l Bacto agar). YNB plates can be used to study amino acid and carbohydrate requirements and for use in this experiment also to test if strains are auxotrophic for adenine.

After three to five days of incubation at 30° C., colonies appeared on the plates, whereas the negative control (i.e., no addition of DNA in the transformation experiment) resulted in blank plates.

Example 5

Plasmid Isolation from Yeast

*S. cerevisiae* colonies from the YNB w/o AA plates were inoculated in 3 ml YephD 24 well plate (BBL Phytone peptone 20.0 g/l, Yeast Extract 10.0 g/l, Sodium Chloride 5.0 g/l, and 2% glucose) and incubated in an INFORS (microtron) incubator ON at 30° C., 80% humidity and 550 rpm. Plasmids were isolated from 2 ml culture. Plasmid isolation from yeast was performed according to a method described in a publication by Kuijpers et al., 2013. This protocol yields sufficient DNA for PCR and transformation to *E. coli*. The plasmids isolated from several yeast colonies were transformed to *E. coli* to further amplify the plasmid and obtain enough DNA for restriction enzyme analysis. One clone having the correct pattern after analysis of the digested plasmid on agarose gel was named MBCAS9/gRSR.

Example 6

Amplification and Purification of the CAS9/gRSR Fragment, Donor DNA and the Hyg Marker Cassette The amplification of the CAS9/gRSR fragment was done with Phusion polymerase (New England Biolabs) according to standard protocols using the forward primer DBC-05793 (SEQ ID NO: 93) and the reverse primer DBC-05796 (SEQ ID NO: 94) and plasmid MBCAS9/gRSR as template. A gBlock fragment was synthesized at IDT (gBlocks® Gene Fragments, Integrated DNA Technologies, Inc) that contains the donor DNA for the desired mutation (SEQ ID NO: 84). PCR amplification of the donor DNA from the gBlock was done with Phusion polymerase (New England Biolabs) according to standard protocols using the forward primer DBC-12197 (SEQ ID NO: 85) and the reverse primer DBC-12198 (SEQ ID NO: 86). A Hygromycin marker cassette (SEQ ID NO: 87) was synthesized at DNA2.0 and delivered in a standard cloning vector. The resulting vector was named CAS159 and used as template in the amplification of the Hygromycin marker cassette using the forward primer DBC-05799 (SEQ ID NO: 88) and reverse primer DBC-05800 (SEQ ID NO: 89). PCR fragments were purified with the PCR purification kit from Macherey Nagel according to the manual. DNA concentration was measured using a NanoDrop (ND-1000 Spectrophotometer, Thermo Scientific).

Example 7

Transformation of *Y. lipolytica* ML324

On day 1, the *Y. lipolytica* strain ML324 is inoculated from a YEPhD-agar plate (BBL Phytone peptone 20.0 g/l, Yeast Extract 10.0 g/l, Sodium Chloride 5.0 g/l, Agar 15.0 g/l and 2% glucose) in 100 ml YephD (BBL Phytone peptone 20.0 g/l, Yeast Extract 10.0 g/l, Sodium Chloride 5.0 g/l, and 2% glucose). Shake flask incubated at 30° C. and 250 rpm.

Transformation of the strain with the PCR amplified fragments was done mainly according to the *S. cerevisiae* transformation protocol described by Gietz and Woods, 2002. Cells were plated after a 20× dilution in YephD-medium on (BBL Phytone peptone 20.0 g/l, Yeast Extract 10.0 g/l, Sodium Chloride 5.0 g/l, 2% glucose) on YEPhD-agar (BBL Phytone peptone 20.0 g/l, Yeast Extract 10.0 g/l, Sodium Chloride 5.0 g/l, Agar 15.0 g/l and 2% glucose) plates with 200 µg/ml Hygromycin B In transformation 1 the following amounts of fragment were used, 3 µg CAS9/gRSR fragment, 3 µg gBlock fragment and 0.3 µg Hygromycin cassette. The amount used in transformation 2 was 3 µg gBlock fragment and 0.3 µg Hygromycin cassette and in transformation 3 no DNA was used.

After 3 to 5 days of incubation at 30° C., colonies appeared on the plates from transformation 1 and 2, whereas transformation plate 3, the negative control (i.e., no addition of DNA in the transformation experiment), resulted in blank plates.

Example 8

Replica Plating of the Transformants to Minimal Media

Obtained transformants were used for replica plating on YNB w/o AA plates (6.7 g/l YNB Difco, BD Becton Dickinson and Company, 20 g/l glucose, 20 g/l Bacto agar) and on YEPhD-agar (BBL Phytone peptone 20.0 g/l, Yeast Extract 10.0 g/l, Sodium Chloride 5.0 g/l, Agar 15.0 g/l and 2% glucose) plates with 200 µg/ml Hygromycin B.

Figure 2:
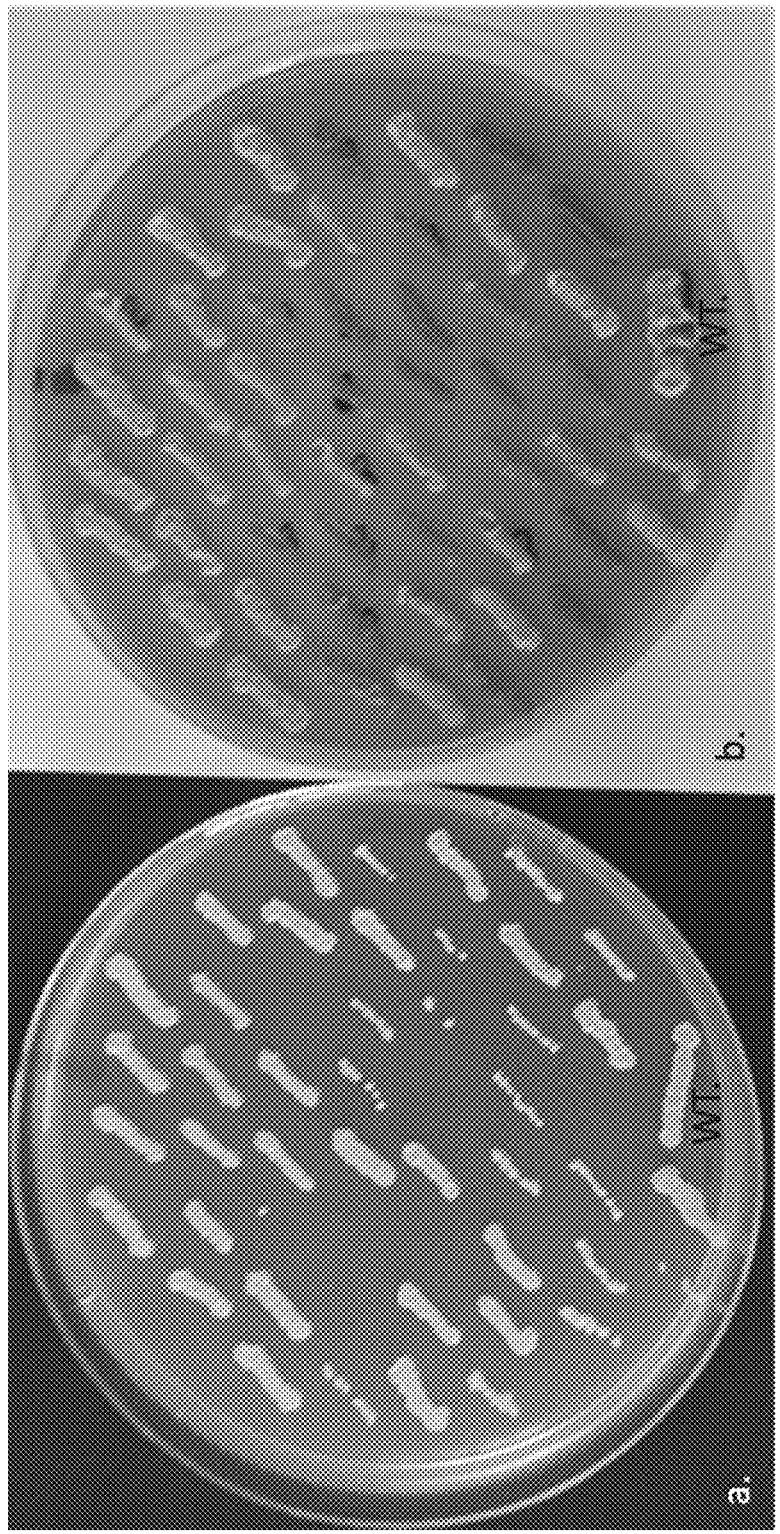
FIG. 2 depicts the results of example 8; replica plating of transformants on minimal media to detect transformants harboring the desired introduced mutation.
Figure 4:
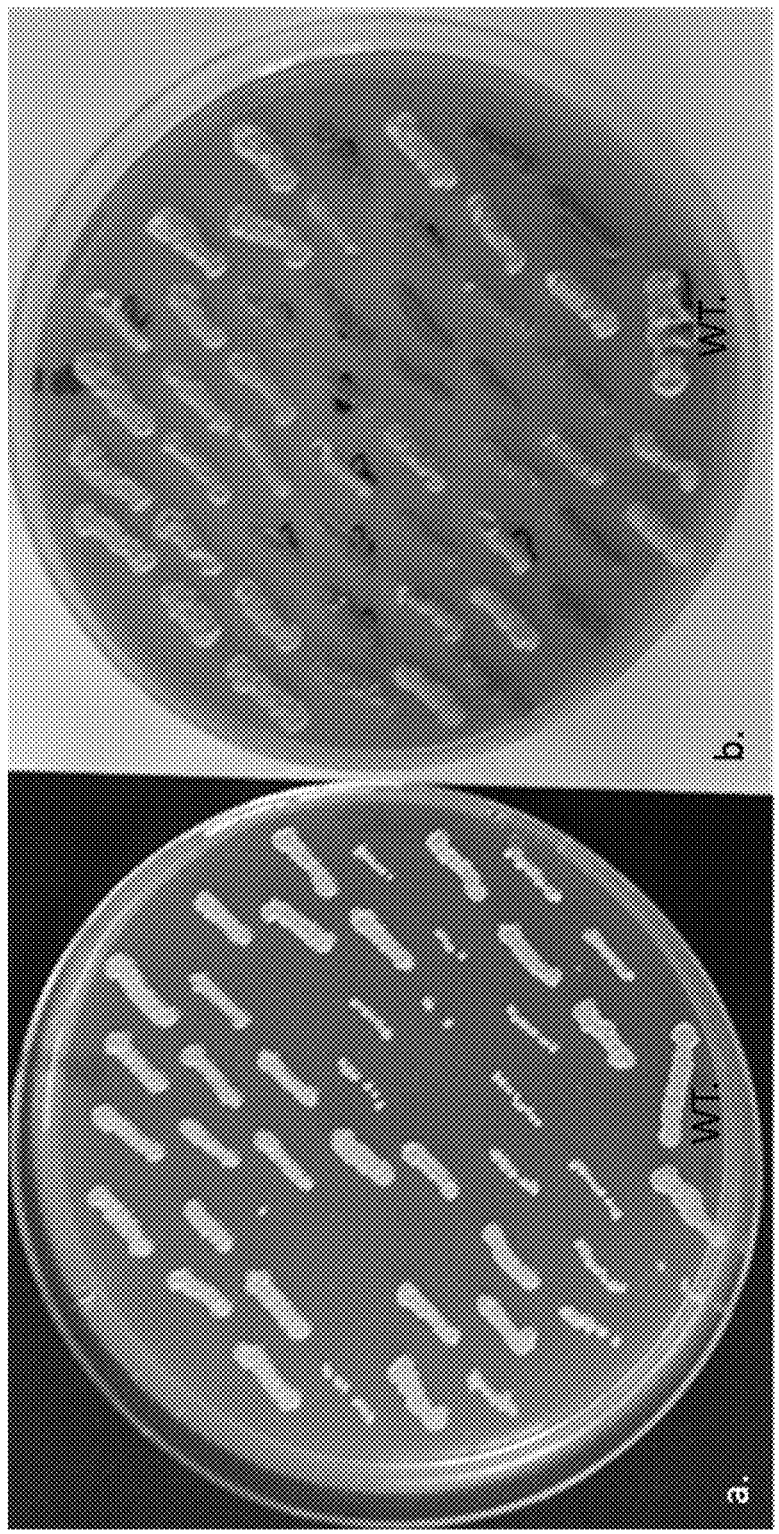

After 2-3 days of incubation at 30° C., colonies started growing on the YephD plates and in some cases also on the YNB w/o AA plates. Further inspection of the plates learned that 4% of the colonies of transformation 2 and 42% of the colonies of transformation 1 were able to grow on YephD but very poor or not on the YNB w/o AA plates which is the expected phenotype after introducing the mutation. In addition a brown colored colony is observed on the YephD plates after a prolonged storage time at 4° C. which is linked to the colonies with poor or no growth on the YNB w/o AA plates (see FIG. 2). The approximately tenfold increase in efficiency of introducing the mutation in the genome of ML324 Y. lipolytica shows the functionality of the CRISPR/CAS9 system. Considering the fact that in this experiment co-transformation of the fragments was used and a percentage of the transformants did not contain all fragments, the efficiency of introducing the genomic mutation in the cells where the CRISPR/CAS9 is present is most likely even higher.

Example 9

Colony PCR SDS/LiAC to Produce DNA Fragment for Sequencing

Colony material of the colonies on the YephD plates were dissolved in a 96 well PCR plate in 100 µl/well 0.2M LiAc/1% SDS. The plate was incubated for 10 minutes at 70° C. The colony mixtures were pipetted to Half Deep Well (HDW)-plates with 300 µl/well EtOH 96% and mixed by pipetting followed by a centrifugation step for 15 minutes at 2750 rpm. The resulting pellet was dried at 55° C. and dissolved in 100 µl TE-buffer. The suspension was centrifuged once more and the supernatant was used as template for amplification of ADE33 sequence fragment. The wild-type sequence is listed as SEQ ID NO:91 and the sequence with the intended mutations is listed as SEQ ID NO: 92 mutation.

The amplification of the ADE33 sequence fragment was done with Phusion polymerase (New England Biolabs) according to standard protocols using the forward primer DBC-12607 (SEQ ID NO: 90) and reverse DBC-12198 (SEQ ID NO: 86). The PCR fragments were purified with the PCR purification kit from Macherey Nagel according to the manual.

Example 10

Sequencing of the Genomic Location

PCR for sequencing was done with BigDye Terminator v3.1 Cycle Sequencing kit of Applied Biosystems according to the manual using the forward primer DBC-12607 (SEQ ID NO:22) and ADE33 sequence fragment as template. Sequencing PCR was cleaned by ethanol/EDTA precipitation according to supplier manual.

ADE33 sequence fragment pellet was dissolved in 10 µl HiDi Formamide of Applied Biosystems and suspension was used for sequence analysis with 3500 Genetic Analyzer of Applied Biosystems (Sanger sequencer).

No mutations were found in the control strains that grew on the YephD plates and on the YNB w/o AA whereas the strains that did not grow on the YNB w/o AA plates showed the intended mutations, namely the introduced stop-codon and mutation of the PAM sequence. Alignment is shown in FIG. 3.

The results show that the CRISPR/CAS9 system was functional in the strains and indeed increased the efficiency of introducing the intended mutations. This knowledge can be used to build an optimized functional CRISPR/CAS9 system for use in Yarrowia lipolytica.

REFERENCES

Aleksenko and Clutterbuck. Fungal Genet. Biol. 1997 21: 373-397. Autonomous plasmid replication in Aspergillus nidulans: AMA1 and MATE elements.

Barnes et al., siRNA as a molecular tool for use in Aspergillus niger (2008) Biotechnology Letters 30 (5): 885-890.

Becker and Guarente, In Abelson, J. N. and Simon, M. I., editors, Guide to Yeast Genetics and Molecular Biology, Methods in Enzymology, Volume 194, 182-187, Academic Press, Inc., New York.

Beetham P R, Kipp P B, Sawycky X L, Arntzen C J and May G D. PNAS 1999, 96, 8774-8778. A tool for functional plant genomics: Chimeric RNA/DNA oligonucleotides cause in vivo gene-specific mutations.

Christianson T W, Sikorski R S, Dante M, Shero J H, Hieter P. Gene. 1992 Jan. 2; 110(1):119-22. Multifunctional yeast high-copy-number shuttle vectors.

Crook N C, Schmitz A C, Alper H S. ACS Synth Biol. 2014 16; 3(5):307-13. Optimization of a yeast RNA interference system for controlling gene expression and enabling rapid metabolic engineering.

DiCarlo J E, Norville J E, Mali P, Rios X, Aach J, Church G M. Nucleic Acids Res. 2013 April; 41(7):4336-43. Genome engineering in Saccharomyces cerevisiae using CRISPR-Cas systems.

Dong C, Beetham P, Vincent K and Sharp P. 2006 Plant Cell Rep 25: 457-465. Oligonucleotide-directed gene repair in wheat using a transient plasmid repair assay system.

Durai S, Mani M, Kandavelou K, Wu J, Porteus M, Chandrasegaran S. Nucleic Acids Res 2005 33 (18): 5978-90. Zinc finger nucleases: custom-designed molecular scissors for genome engineering of plant and mammalian cells.

Gaj T, Gersbach, C and Barbas C. Trends in Biotechnology, 2013, Vol. 31, No. 7 397-405. ZFN, TALEN, and CRISPR/Cas-based methods for genome engineering.

Gao Y and Zhao Y. J Integr Plant Biol. 2014 April; 56(4): 343-9. Self-processing of ribozyme-flanked RNAs into guide RNAs in vitro and in vivo for CRISPR-mediated genome editing.

Gietz R D, Woods R A. Methods Enzymol. 2002; 350:87-96. Transformation of yeast by lithium acetate/single-stranded carrier DNA/polyethylene glycol method.

Goldstein, A. L., and McCusker, J. H. Yeast 1999. 15, 1541-15. Three new dominant drug resistance cassettes for gene disruption in Saccharomyces cerevisiae.

Guilinger J P, Thompson D B, Liu D R. Nat Biotechnol. 2014 577-582. Fusion of catalytically inactive Cas9 to FokI nuclease improves the specificity of genome modification.

Güldener, U., Heck, S., Fiedler, T., Beinhauer, J., and Hegemann, J. H. Nucleic Acids Research 1996. 24, 2519-2524. A new efficient gene disruption cassette for repeated use in budding yeast.

Hsu P D, Lander E S, Zhang F. Cell. 2014 Jun. 5; 157(6): 1262-78. Development and applications of CRISPR-Cas9 for genome engineering.

Ito et al., 1983, Journal of Bacteriology 153: 163.

Jacobs J Z, Ciccaglione K M, Tournier V, Zaratiegui M. Nat Commun. 2014 Oct. 29; 5:5344. Implementation of the CRISPR-Cas9 system in fission yeast.

Jørgensen T R, Park J, Arentshorst M, van Welzen A M, Lamers G, Vankuyk P A, Damveld R A, van den Hondel C A, Nielsen K F, Frisvad J C, Ram A F. Fungal Genet Biol. 2011 May; 48(5):544-53. The molecular and genetic basis of conidial pigmentation in *Aspergillus niger*.

Kornberg R. Trends in Cell Biology 1999 9 (12): M46 Eukaryotic transcriptional control.

Kuijpers et al. Microbial Cell Factories 2013, 12:47. A versatile, efficient strategy for assembly of multi-fragment expression vectors in *Saccharomyces cerevisiae* using 60 bp synthetic recombination sequences.

Larson, M. H.; Gilbert, L. A.; Wang, X; Lim, W. A.; Weissman, J. S.; Qi, L. S. Nature Protocols 2013 8 (11) 2180-96. CRISPR interference (CRISPRi) for sequence-specific control of gene expression.

Lõoke M, Kristjuhan K, Kristjuhan A. Biotechniques. 2011 May; 50(5):325-8. Extraction of genomic DNA from yeasts for PCR-based applications.

Mali P, Yang L, Esvelt K M, Aach J, Guell M, DiCarlo J E, Norville J E, Church G M. Science. 2013 Feb. 15; 339(6121):823-6. RNA-guided human genome engineering via Cas9.

Marck C, Kachouri-Lafond R, Lafontaine I, Westhof E, Dujon B, Grosjean H. Nucleic Acids Res. 2006 Apr. 5; 34(6):1816-35. The RNA polymerase III-dependent family of genes in hemiascomycetes: comparative RNomics, decoding strategies, transcription and evolutionary implications.

Mouyna I, Henry C, Doering T L, Latgé J P. FEMS Microbiol Lett. 2004 Aug. 15; 237(2):317-24. Gene silencing with RNA interference in the human pathogenic fungus *Aspergillus fumigatus*.

Nakamura, Y., et al. Nucl. Acids Res. 2000 28:292. Codon usage tabulated from the international DNA sequence databases: status for the year 2000.

Oliveira et al., Efficient cloning system for construction of gene silencing vectors in *Aspergillus niger* (2008) Appl. Microbiol. and Biotechnol. 80 (5): 917-924.

Ran F A, Hsu P D, Lin C Y, Gootenberg J S, Konermann S, Trevino A E, Scott D A, Inoue A, Matoba S, Zhang Y, Zhang F. Cell 2013 154, 1380-1389. Double nicking by RNA-guided CRISPR Cas9 for enhanced genome editing specificity.

Sander J D, Joung J K. Nat Biotechnol. 2014 April; 32(4): 347-55. doi: 10.1038/nbt.2842. Epub 2014 Mar. 2. CRISPR-Cas systems for editing, regulating and targeting genomes.

Sikorski R S, Hieter P. Genetics. 1989 May; 122(1):19-27. A system of shuttle vectors and yeast host strains designed for efficient manipulation of DNA in *Saccharomyces cerevisiae*.

Ryan O W, Skerker J M, Maurer M J, Li X, Tsai J C, Poddar S, Lee M E, DeLoache W, Dueber J E, Arkin A P, Cate J H. Elife. 2014. 19; 3. 03703.

Tsai S Q, Wyvekens N, Khayter C, et al. Nat Biotechnol. 2014 32(6):569-576. Dimeric CRISPR RNA-guided FokI nucleases for highly specific genome editing.

Wah, D. A.; J. Bitinaite, Schildkraut, I., Aggarwal, A. K. Proc Natl Acad Sci USA 1998 95 (18): 10564-9. Structure of FokI has implications for DNA cleavage.

Zhang G, Kong I, Kim H, Liu J, Cate J H, Jin Y S. Appl Environ Microbiol. 2014 Dec. 15; 80(24):7694-701. doi: 10.1128/AEM.02310-14. Epub 2014 Oct. 3. Construction of a quadruple auxotrophic mutant of an industrial polyploidy *Saccharomyces cerevisiae* using RNA-guided Cas9 nuclease.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10590436B2). An electronic copy of the "Sequence Listing" will also be available from the USPTO upon request and payment of the fee set forth in 37 CFR 1.19(b)(3).

The invention claimed is:

1. A non-naturally occurring or engineered composition comprising a CRISPR-Cas system comprising guide-polynucleotide and a Cas protein, wherein the guide-polynucleotide comprises a guide-sequence that is the reverse complement of a target-polynucleotide sequence in a host cell, which host cell is a *Yarrowia lipolytic* yeast, wherein the guide-polynucleotide directs binding of the Cas protein at the target-polynucleotide in the host cell to form a CRISPR-Cas complex, wherein the guide-polynucleotide sequence is the reverse complement of the (N)y part of a 5'-(N)yPAM-3' polynucleotide sequence target in the genome of the host cell, wherein y is an integer of 8-30, wherein PAM is a protospacer adjacent motif, wherein PAM is a sequence selected from the group consisting of 5'-XGG-3', 5'-XGGXG-3', 5'-XXAGAAW-3', 5'-XXXXGATT-3', 5'-XXAGAA-3', 5'-XAAAAC-3', wherein X can be any nucleotide; and W is A or T, wherein the guide-polynucleotide is encoded by a polynucleotide that is operably linked to an RNA polymerase II promoter, wherein the polynucleotide that is operably linked to an RNA polymerase II promoter further encodes a pre-guide polynucleotide comprising the guide-polynucleotide and at least one self-processing ribozyme, wherein, when transcribed, the guide-polynucleotide is released by the self-processing ribozyme from the pre-guide-polynucleotide transcript.

2. A composition according to claim 1, wherein the Cas protein is encoded by a polynucleotide.

3. A composition according to claim 2, wherein the polynucleotides encoding the guide-polynucleotides and the polynucleotide encoding the Cas protein are comprised in one vector.

4. A composition according to claim 3, wherein the vector is linear.

5. A composition according to claim 4, comprising at least two distinct polynucleotides each encoding a distinct guide-polynucleotide, wherein said at least two polynucleotides additionally comprise sequence identity with each other such that recombination of the polynucleotides encoding the distinct guide-polynucleotides and said vector is facilitated, wherein the recombination optionally is in vivo recombination in the host cell.

6. A composition according to claim 2, wherein the polynucleotide encoding the guide-polynucleotide and the polynucleotide encoding the Cas protein are comprised in separate vectors.

7. A composition according to claim 6, the vector comprising the polynucleotide encoding the Cas protein is a low copy number vector and the vector comprising the polynucleotide encoding the guide-polynucleotide is a high copy number vector.

8. A composition according to claim 7, wherein one or more or vectors comprise a selectable marker, optionally, wherein each vector comprises a distinct selectable marker.

9. A composition according to claim 1, further comprising one or more distinct exogenous polynucleotides that upon cleavage of the target-polynucleotide by the CRISPR-Cas complex recombines with the target-polynucleotide, resulting in a modified target-polynucleotide.

10. A composition according to claim 9, wherein at least two distinct exogenous polynucleotides are present that upon cleavage of the target-polynucleotide by the CRISPR-Cas complex recombine with the target-polynucleotides, resulting in a modified target-polynucleotide, wherein said at least two distinct exogenous polynucleotides comprise sequence identity with each other such that recombination of said distinct exogenous polynucleotides is facilitated, wherein the recombination optionally is in vivo recombination in the host cell.

11. A composition according to claim 9, wherein a further and distinct exogenous polynucleotide is present that upon cleavage of the target-polynucleotide by the CRISPR-Cas complex recombines with the target-polynucleotide, resulting in a modified target-polynucleotide, wherein an additional polynucleotide is present that has sequence identity with the exogenous and distinct polynucleotides such that recombination of the exogenous and distinct polynucleotides is facilitated, and wherein the recombination optionally is in vivo recombination in the host cell.

12. A composition according to claim 9, wherein one or more exogenous polynucleotides are operably linked to the guide-polynucleotide.

13. A composition according to claim 3, wherein the vector is an autonomously replicating vector.

14. A composition according to claim 1, wherein the Cas protein comprises at least one nuclear localization sequence, optionally a heterologous nuclear localization sequence.

15. A composition according to claim 1, wherein the Cas protein has activity for directing cleavage of both polynucleotide strands at the location of the target-sequence.

16. A composition according to claim 1, wherein the Cas protein comprises at least one mutation, such that the protein has altered nuclease activity compared to the corresponding wild-type Cas protein, optionally having activity to direct cleavage of a single polynucleotide strand at the location of the target-sequence.

17. A composition according to claim 1, wherein the Cas protein encoding polynucleotide is codon optimized for the host cell, optionally codon pair optimized.

18. A host cell comprising a composition according to claim 1.

19. The composition according to claim 1, wherein the *Yarrowia* is *Yarrowia lipolytica* deposited under number ATCC18943.

* * * * *